US011629169B2

(12) United States Patent
Cho et al.

(10) Patent No.: US 11,629,169 B2
(45) Date of Patent: Apr. 18, 2023

(54) USE OF PEPTIDES AS THERAPEUTIC AGENT FOR AUTOIMMUNE DISEASES AND BONE DISEASES

(71) Applicant: KINE SCIENCES CO., LTD., Seoul (KR)

(72) Inventors: Dae Ho Cho, Seoul (KR); Kyung Eun Kim, Seoul (KR); Myun Soo Kim, Seoul (KR); Sun Young Park, Seoul (KR); Hee Young Jung, Seoul (KR)

(73) Assignee: KINE SCIENCES CO., LTD., Seoul (KR)

( * ) Notice: Subject to any disclaimer, the term of this patent is extended or adjusted under 35 U.S.C. 154(b) by 215 days.

(21) Appl. No.: 16/646,069

(22) PCT Filed: Sep. 14, 2018

(86) PCT No.: PCT/KR2018/010873
§ 371 (c)(1),
(2) Date: Mar. 10, 2020

(87) PCT Pub. No.: WO2019/054808
PCT Pub. Date: Mar. 21, 2019

(65) Prior Publication Data
US 2020/0283477 A1  Sep. 10, 2020

(30) Foreign Application Priority Data

Sep. 15, 2017 (KR) .................... 10-2017-0118947
Sep. 15, 2017 (KR) .................... 10-2017-0118949
Sep. 14, 2018 (KR) .................... 10-2018-0110473
Sep. 14, 2018 (KR) .................... 10-2018-0110480

(51) Int. Cl.
*C07K 5/097* (2006.01)
*A61P 37/06* (2006.01)
*A61P 19/02* (2006.01)
*A61K 38/00* (2006.01)

(52) U.S. Cl.
CPC ............ *C07K 5/0821* (2013.01); *A61P 19/02* (2018.01); *A61P 37/06* (2018.01); *A61K 38/00* (2013.01)

(58) Field of Classification Search
CPC .... C07K 5/0821; C07K 5/081; C07K 5/0823; C07K 14/001; C07K 7/06; C07K 7/08; A61P 19/02; A61P 37/06; A61P 29/00; A61K 38/00; A61K 38/06; Y02P 20/55; A23L 33/18
See application file for complete search history.

(56) References Cited

U.S. PATENT DOCUMENTS

| 6,864,284 B2 * | 3/2005 | Roomi ............... A61P 43/00 514/474 |
| 2009/0238895 A1 * | 9/2009 | Pierzynowski ........ A61K 33/26 424/646 |
| 2011/0143993 A1 | 6/2011 | Langer et al. |
| 2014/0087997 A1 | 3/2014 | Adir et al. |

FOREIGN PATENT DOCUMENTS

| KR | 1020140005110 | 1/2014 |
| WO | 2016204841 | 12/2016 |
| WO | 2017155233 | 9/2017 |

OTHER PUBLICATIONS

Biswadip Banerji, et al., "Formation of Annular Protofibrillar Assembly by Cysteine Tripeptide: Unraveling the Interactions with NMR, FTIR, and Molecular Dynamics", J. Phys. Chem. B, (2017), vol. 121, pp. 6367-6379.
David D Brand, et al., "Collagen-induced arthritis", Nature Protocols, vol. 2, No. 5, (2007), pp. 1269-1275.
Laura Connell, et al., "New cytokine targets in inflammatory rheumatic diseases", Best Practice & Research Clinical Rheumatology, vol. 20, No. 5, (2006), pp. 865-878.
Lois T. Hunt, et al., "The Occurrence in Proteins of the Tripeptides ASN-X-SER and ASN-X-THR and of Bound Carbohydrate", Biochemical and Biophysical Research Communications, vol. 39, No. 4, (1970), p. 757-765.
Marianne T. Bauer, et al., "Formation of b-sheets in glutamine and alanine tripeptides", Biochemical and Biophysical Research Communications, vol. 406, (2011), pp. 348-352.
Martine Chabaud, et al., "The Combination of Tumor Necrosis Factor a Blockade With Interleukin-1 and Interleukin-17 Blockade Is More Effective for Controlling Synovial Inflammation and Bone Resorption in an Ex Vivo Model", Arthritis & Rheumatism, vol. 44, No. 6, (Jun. 2001), pp. 1293-1303.
Mary E. Krause, et al., "Novel Tripeptide Model of Nickel Superoxide Dismutase", Inorg. Chem., (2010), vol. 49, pp. 362-364.
R. Natasha Grewal, et al., "Fragmentation of Protonated Tripeptides: The Proline Effect Revisited", J. Phys. Chem. B, (2004), vol. 108, pp. 4899-4908.
Sharmila Anishetty, et al., "Tripeptide analysis of protein structures", BMC Structural Biology, (2002), vol. 2, No. 9, pp. 1-8.

* cited by examiner

*Primary Examiner* — Marcela M Cordero Garcia
(74) *Attorney, Agent, or Firm* — Cantor Colburn LLP

(57) ABSTRACT

The present invention relates to use of peptides as a therapeutic agent, wherein it has been confirmed that the peptides of the present invention significantly inhibit the activity of T cells and the differentiation of T helper 17 cells (Th17 cells), which are associated with autoimmune disease, and have remarkable effects of treating and improving arthritis in an animal model of arthritis. Therefore, the peptides may be used as an active ingredient in therapeutic agents for various autoimmune diseases such as bone disease, inflammatory disease or rheumatoid arthritis.

6 Claims, 8 Drawing Sheets
Specification includes a Sequence Listing.

Relative Arthritis Score (%)

|         | 15 | 17 | 19 | 21   | 24   | 26  | 28   |
|---------|----|----|----|------|------|-----|------|
| Normal  | 0  | 0  | 0  | 0    | 0    | 0   | 0    |
| Vehicle (PBS) | 0 | 50 | 50 | 62.5 | 87.5 | 100 | 100 |
| MTX     | 0  | 0  | 0  | 0    | 12.5 | 50  | 50   |
| Pep1    | 0  | 0  | 0  | 0    | 0    | 0   | 12.5 |

Representative diagram

Relative Arthritis Score (%)

|  | 15 | 17 | 19 | 21 | 24 | 26 | 28 |
|---|---|---|---|---|---|---|---|
| Normal | 0 | 0 | 0 | 0 | 0 | 0 | 0 |
| Vehicle (PBS) | 0 | 50 | 50 | 62.5 | 87.5 | 100 | 100 |
| MTX | 0 | 0 | 0 | 0 | 12.5 | 50 | 50 |
| Pep2 | 0 | 12.5 | 25 | 25 | 25 | 25 | 25 |

Representative diagram

Relative Arthritis Score (%)

|         | 15 | 17 | 19 | 21   | 24   | 26  | 28  |
|---------|----|----|----|------|------|-----|-----|
| Normal  | 0  | 0  | 0  | 0    | 0    | 0   | 0   |
| Vehicle (PBS) | 0 | 50 | 50 | 62.5 | 87.5 | 100 | 100 |
| MTX     | 0  | 0  | 0  | 0    | 12.5 | 50  | 50  |
| Pep4    | 0  | 0  | 25 | 25   | 25   | 25  | 25  |

Representative diagram

Relative Arthritis Score (%)

|  | 15 | 17 | 19 | 21 | 24 | 26 | 28 |
|---|---|---|---|---|---|---|---|
| Normal | 0 | 0 | 0 | 0 | 0 | 0 | 0 |
| Vehicle (PBS) | 0 | 50 | 50 | 62.5 | 87.5 | 100 | 100 |
| MTX | 0 | 0 | 0 | 0 | 12.5 | 50 | 50 |
| Pep6 | 0 | 0 | 0 | 0 | 12.5 | 12.5 | 12.5 |

Representative diagram

SEQUENCE LISTING

<160> NUMBER OF SEQ ID NOS: 106

<210> SEQ ID NO 1
<211> LENGTH: 3
<212> TYPE: PRT
<213> ORGANISM: Artificial Sequence
<220> FEATURE:
<223> OTHER INFORMATION: PEPTIDE1
<220> FEATURE:
<221> NAME/KEY: MISC_FEATURE
<222> LOCATION: (1)..(3)
<223> OTHER INFORMATION: Xaa is Proline, Serine, Threonine, Glutamine,
      Asparagine or Cysteine

<400> SEQUENCE: 1

Xaa Xaa Xaa
1

<210> SEQ ID NO 2
<211> LENGTH: 3
<212> TYPE: PRT
<213> ORGANISM: Artificial Sequence
<220> FEATURE:
<223> OTHER INFORMATION: PSP1

<400> SEQUENCE: 2

Pro Ser Pro
1

<210> SEQ ID NO 3
<211> LENGTH: 3
<212> TYPE: PRT
<213> ORGANISM: Artificial Sequence
<220> FEATURE:
<223> OTHER INFORMATION: Synthetic peptide 1

<400> SEQUENCE: 3

Pro Pro Ser
1

<210> SEQ ID NO 4
<211> LENGTH: 3
<212> TYPE: PRT
<213> ORGANISM: Artificial Sequence
<220> FEATURE:
<223> OTHER INFORMATION: Synthetic peptide 2

<400> SEQUENCE: 4

Pro Pro Thr
1

<210> SEQ ID NO 5
<211> LENGTH: 3
<212> TYPE: PRT
<213> ORGANISM: Artificial Sequence
<220> FEATURE:
<223> OTHER INFORMATION: Synthetic peptide 3

<400> SEQUENCE: 5

Pro Pro Gln
1

<210> SEQ ID NO 6
<211> LENGTH: 3
<212> TYPE: PRT
<213> ORGANISM: Artificial Sequence
<220> FEATURE:
<223> OTHER INFORMATION: Synthetic peptide 4

```
<400> SEQUENCE: 6

Pro Pro Asn
1

<210> SEQ ID NO 7
<211> LENGTH: 3
<212> TYPE: PRT
<213> ORGANISM: Artificial Sequence
<220> FEATURE:
<223> OTHER INFORMATION: Synthetic peptide 5

<400> SEQUENCE: 7

Pro Ser Ser
1

<210> SEQ ID NO 8
<211> LENGTH: 3
<212> TYPE: PRT
<213> ORGANISM: Artificial Sequence
<220> FEATURE:
<223> OTHER INFORMATION: Synthetic peptide 6

<400> SEQUENCE: 8

Pro Ser Thr
1

<210> SEQ ID NO 9
<211> LENGTH: 3
<212> TYPE: PRT
<213> ORGANISM: Artificial Sequence
<220> FEATURE:
<223> OTHER INFORMATION: Synthetic peptide 7

<400> SEQUENCE: 9

Pro Ser Gln
1

<210> SEQ ID NO 10
<211> LENGTH: 3
<212> TYPE: PRT
<213> ORGANISM: Artificial Sequence
<220> FEATURE:
<223> OTHER INFORMATION: Synthetic peptide 8

<400> SEQUENCE: 10

Pro Ser Asn
1

<210> SEQ ID NO 11
<211> LENGTH: 3
<212> TYPE: PRT
<213> ORGANISM: Artificial Sequence
<220> FEATURE:
<223> OTHER INFORMATION: Synthetic peptide 9

<400> SEQUENCE: 11

Pro Ser Cys
1

<210> SEQ ID NO 12
<211> LENGTH: 3
<212> TYPE: PRT
<213> ORGANISM: Artificial Sequence
<220> FEATURE:
<223> OTHER INFORMATION: Synthetic peptide 10
```

```
<400> SEQUENCE: 12

Pro Thr Pro
1

<210> SEQ ID NO 13
<211> LENGTH: 3
<212> TYPE: PRT
<213> ORGANISM: Artificial Sequence
<220> FEATURE:
<223> OTHER INFORMATION: Synthetic peptide 11

<400> SEQUENCE: 13

Pro Thr Ser
1

<210> SEQ ID NO 14
<211> LENGTH: 3
<212> TYPE: PRT
<213> ORGANISM: Artificial Sequence
<220> FEATURE:
<223> OTHER INFORMATION: Synthetic peptide 12

<400> SEQUENCE: 14

Pro Thr Thr
1

<210> SEQ ID NO 15
<211> LENGTH: 3
<212> TYPE: PRT
<213> ORGANISM: Artificial Sequence
<220> FEATURE:
<223> OTHER INFORMATION: Synthetic peptide 13

<400> SEQUENCE: 15

Pro Thr Gln
1

<210> SEQ ID NO 16
<211> LENGTH: 3
<212> TYPE: PRT
<213> ORGANISM: Artificial Sequence
<220> FEATURE:
<223> OTHER INFORMATION: Synthetic peptide 14

<400> SEQUENCE: 16

Pro Thr Asn
1

<210> SEQ ID NO 17
<211> LENGTH: 3
<212> TYPE: PRT
<213> ORGANISM: Artificial Sequence
<220> FEATURE:
<223> OTHER INFORMATION: Synthetic peptide 15

<400> SEQUENCE: 17

Pro Thr Cys
1

<210> SEQ ID NO 18
<211> LENGTH: 3
<212> TYPE: PRT
<213> ORGANISM: Artificial Sequence
<220> FEATURE:
<223> OTHER INFORMATION: Synthetic peptide 16

<400> SEQUENCE: 18
```

Pro Gln Pro
1

<210> SEQ ID NO 19
<211> LENGTH: 3
<212> TYPE: PRT
<213> ORGANISM: Artificial Sequence
<220> FEATURE:
<223> OTHER INFORMATION: Synthetic peptide 17

<400> SEQUENCE: 19

Pro Gln Ser
1

<210> SEQ ID NO 20
<211> LENGTH: 3
<212> TYPE: PRT
<213> ORGANISM: Artificial Sequence
<220> FEATURE:
<223> OTHER INFORMATION: Synthetic peptide 18

<400> SEQUENCE: 20

Pro Gln Thr
1

<210> SEQ ID NO 21
<211> LENGTH: 3
<212> TYPE: PRT
<213> ORGANISM: Artificial Sequence
<220> FEATURE:
<223> OTHER INFORMATION: Synthetic peptide 19

<400> SEQUENCE: 21

Pro Gln Asn
1

<210> SEQ ID NO 22
<211> LENGTH: 3
<212> TYPE: PRT
<213> ORGANISM: Artificial Sequence
<220> FEATURE:
<223> OTHER INFORMATION: Synthetic peptide 20

<400> SEQUENCE: 22

Pro Gln Cys
1

<210> SEQ ID NO 23
<211> LENGTH: 3
<212> TYPE: PRT
<213> ORGANISM: Artificial Sequence
<220> FEATURE:
<223> OTHER INFORMATION: Synthetic peptide 21

<400> SEQUENCE: 23

Pro Asn Pro
1

<210> SEQ ID NO 24
<211> LENGTH: 3
<212> TYPE: PRT
<213> ORGANISM: Artificial Sequence
<220> FEATURE:
<223> OTHER INFORMATION: Synthetic peptide 22

<400> SEQUENCE: 24

Pro Asn Ser
1

<210> SEQ ID NO 25
<211> LENGTH: 3
<212> TYPE: PRT
<213> ORGANISM: Artificial Sequence
<220> FEATURE:
<223> OTHER INFORMATION: Synthetic peptide 23

<400> SEQUENCE: 25

Pro Asn Thr
1

<210> SEQ ID NO 26
<211> LENGTH: 3
<212> TYPE: PRT
<213> ORGANISM: Artificial Sequence
<220> FEATURE:
<223> OTHER INFORMATION: Synthetic peptide 24

<400> SEQUENCE: 26

Pro Asn Gln
1

<210> SEQ ID NO 27
<211> LENGTH: 3
<212> TYPE: PRT
<213> ORGANISM: Artificial Sequence
<220> FEATURE:
<223> OTHER INFORMATION: Synthetic peptide 25

<400> SEQUENCE: 27

Pro Asn Asn
1

<210> SEQ ID NO 28
<211> LENGTH: 3
<212> TYPE: PRT
<213> ORGANISM: Artificial Sequence
<220> FEATURE:
<223> OTHER INFORMATION: Synthetic peptide 26

<400> SEQUENCE: 28

Pro Asn Cys
1

<210> SEQ ID NO 29
<211> LENGTH: 3
<212> TYPE: PRT
<213> ORGANISM: Artificial Sequence
<220> FEATURE:
<223> OTHER INFORMATION: Synthetic peptide 27

<400> SEQUENCE: 29

Pro Cys Pro
1

<210> SEQ ID NO 30
<211> LENGTH: 3
<212> TYPE: PRT
<213> ORGANISM: Artificial Sequence
<220> FEATURE:
<223> OTHER INFORMATION: Synthetic peptide 28

<400> SEQUENCE: 30

Pro Cys Ser

```
<210> SEQ ID NO 31
<211> LENGTH: 3
<212> TYPE: PRT
<213> ORGANISM: Artificial Sequence
<220> FEATURE:
<223> OTHER INFORMATION: Synthetic peptide 29

<400> SEQUENCE: 31

Pro Cys Thr
1

<210> SEQ ID NO 32
<211> LENGTH: 3
<212> TYPE: PRT
<213> ORGANISM: Artificial Sequence
<220> FEATURE:
<223> OTHER INFORMATION: Synthetic peptide 30

<400> SEQUENCE: 32

Pro Cys Gln
1

<210> SEQ ID NO 33
<211> LENGTH: 3
<212> TYPE: PRT
<213> ORGANISM: Artificial Sequence
<220> FEATURE:
<223> OTHER INFORMATION: Synthetic peptide 31

<400> SEQUENCE: 33

Pro Cys Asn
1

<210> SEQ ID NO 34
<211> LENGTH: 3
<212> TYPE: PRT
<213> ORGANISM: Artificial Sequence
<220> FEATURE:
<223> OTHER INFORMATION: Synthetic peptide 32

<400> SEQUENCE: 34

Pro Cys Cys
1

<210> SEQ ID NO 35
<211> LENGTH: 3
<212> TYPE: PRT
<213> ORGANISM: Artificial Sequence
<220> FEATURE:
<223> OTHER INFORMATION: Synthetic peptide 33

<400> SEQUENCE: 35

Ser Ser Pro
1

<210> SEQ ID NO 36
<211> LENGTH: 3
<212> TYPE: PRT
<213> ORGANISM: Artificial Sequence
<220> FEATURE:
<223> OTHER INFORMATION: Synthetic peptide 34

<400> SEQUENCE: 36

Ser Pro Ser
1
```

```
<210> SEQ ID NO 37
<211> LENGTH: 3
<212> TYPE: PRT
<213> ORGANISM: Artificial Sequence
<220> FEATURE:
<223> OTHER INFORMATION: Synthetic peptide 35

<400> SEQUENCE: 37

Ser Pro Thr
1

<210> SEQ ID NO 38
<211> LENGTH: 3
<212> TYPE: PRT
<213> ORGANISM: Artificial Sequence
<220> FEATURE:
<223> OTHER INFORMATION: Synthetic peptide 36

<400> SEQUENCE: 38

Ser Pro Gln
1

<210> SEQ ID NO 39
<211> LENGTH: 3
<212> TYPE: PRT
<213> ORGANISM: Artificial Sequence
<220> FEATURE:
<223> OTHER INFORMATION: Synthetic peptide 37

<400> SEQUENCE: 39

Ser Pro Asn
1

<210> SEQ ID NO 40
<211> LENGTH: 3
<212> TYPE: PRT
<213> ORGANISM: Artificial Sequence
<220> FEATURE:
<223> OTHER INFORMATION: Synthetic peptide 38

<400> SEQUENCE: 40

Ser Thr Pro
1

<210> SEQ ID NO 41
<211> LENGTH: 3
<212> TYPE: PRT
<213> ORGANISM: Artificial Sequence
<220> FEATURE:
<223> OTHER INFORMATION: Synthetic peptide 39

<400> SEQUENCE: 41

Ser Thr Ser
1

<210> SEQ ID NO 42
<211> LENGTH: 3
<212> TYPE: PRT
<213> ORGANISM: Artificial Sequence
<220> FEATURE:
<223> OTHER INFORMATION: Synthetic peptide 40

<400> SEQUENCE: 42

Thr Pro Pro
1
```

```
<210> SEQ ID NO 43
<211> LENGTH: 3
<212> TYPE: PRT
<213> ORGANISM: Artificial Sequence
<220> FEATURE:
<223> OTHER INFORMATION: Synthetic peptide 41

<400> SEQUENCE: 43

Thr Pro Ser
1

<210> SEQ ID NO 44
<211> LENGTH: 3
<212> TYPE: PRT
<213> ORGANISM: Artificial Sequence
<220> FEATURE:
<223> OTHER INFORMATION: Synthetic peptide 42

<400> SEQUENCE: 44

Thr Ser Pro
1

<210> SEQ ID NO 45
<211> LENGTH: 3
<212> TYPE: PRT
<213> ORGANISM: Artificial Sequence
<220> FEATURE:
<223> OTHER INFORMATION: Synthetic peptide 43

<400> SEQUENCE: 45

Thr Ser Ser
1

<210> SEQ ID NO 46
<211> LENGTH: 6
<212> TYPE: PRT
<213> ORGANISM: Artificial Sequence
<220> FEATURE:
<223> OTHER INFORMATION: Synthetic peptide 44

<400> SEQUENCE: 46

Pro Pro Ser Pro Pro Ser
1               5

<210> SEQ ID NO 47
<211> LENGTH: 6
<212> TYPE: PRT
<213> ORGANISM: Artificial Sequence
<220> FEATURE:
<223> OTHER INFORMATION: Synthetic peptide 45

<400> SEQUENCE: 47

Pro Pro Thr Pro Pro Thr
1               5

<210> SEQ ID NO 48
<211> LENGTH: 6
<212> TYPE: PRT
<213> ORGANISM: Artificial Sequence
<220> FEATURE:
<223> OTHER INFORMATION: Synthetic peptide 46

<400> SEQUENCE: 48

Pro Pro Gln Pro Pro Gln
1               5
```

```
<210> SEQ ID NO 49
<211> LENGTH: 6
<212> TYPE: PRT
<213> ORGANISM: Artificial Sequence
<220> FEATURE:
<223> OTHER INFORMATION: Synthetic peptide 47

<400> SEQUENCE: 49

Pro Pro Asn Pro Pro Asn
1               5

<210> SEQ ID NO 50
<211> LENGTH: 6
<212> TYPE: PRT
<213> ORGANISM: Artificial Sequence
<220> FEATURE:
<223> OTHER INFORMATION: Synthetic peptide 48

<400> SEQUENCE: 50

Pro Ser Ser Pro Ser Ser
1               5

<210> SEQ ID NO 51
<211> LENGTH: 6
<212> TYPE: PRT
<213> ORGANISM: Artificial Sequence
<220> FEATURE:
<223> OTHER INFORMATION: Synthetic peptide 49

<400> SEQUENCE: 51

Pro Ser Thr Pro Ser Thr
1               5

<210> SEQ ID NO 52
<211> LENGTH: 6
<212> TYPE: PRT
<213> ORGANISM: Artificial Sequence
<220> FEATURE:
<223> OTHER INFORMATION: Synthetic peptide 50

<400> SEQUENCE: 52

Pro Ser Gln Pro Ser Gln
1               5

<210> SEQ ID NO 53
<211> LENGTH: 6
<212> TYPE: PRT
<213> ORGANISM: Artificial Sequence
<220> FEATURE:
<223> OTHER INFORMATION: Synthetic peptide 51

<400> SEQUENCE: 53

Pro Ser Asn Pro Ser Asn
1               5

<210> SEQ ID NO 54
<211> LENGTH: 6
<212> TYPE: PRT
<213> ORGANISM: Artificial Sequence
<220> FEATURE:
<223> OTHER INFORMATION: Synthetic peptide 52

<400> SEQUENCE: 54

Pro Ser Cys Pro Ser Cys
1               5

<210> SEQ ID NO 55
```

```
<211> LENGTH: 6
<212> TYPE: PRT
<213> ORGANISM: Artificial Sequence
<220> FEATURE:
<223> OTHER INFORMATION: Synthetic peptide 53

<400> SEQUENCE: 55

Pro Thr Pro Pro Thr Pro
1               5

<210> SEQ ID NO 56
<211> LENGTH: 6
<212> TYPE: PRT
<213> ORGANISM: Artificial Sequence
<220> FEATURE:
<223> OTHER INFORMATION: Synthetic peptide 54

<400> SEQUENCE: 56

Pro Thr Ser Pro Thr Ser
1               5

<210> SEQ ID NO 57
<211> LENGTH: 6
<212> TYPE: PRT
<213> ORGANISM: Artificial Sequence
<220> FEATURE:
<223> OTHER INFORMATION: Synthetic peptide 55

<400> SEQUENCE: 57

Pro Thr Thr Pro Thr Thr
1               5

<210> SEQ ID NO 58
<211> LENGTH: 6
<212> TYPE: PRT
<213> ORGANISM: Artificial Sequence
<220> FEATURE:
<223> OTHER INFORMATION: Synthetic peptide 56

<400> SEQUENCE: 58

Ser Ser Pro Ser Ser Pro
1               5

<210> SEQ ID NO 59
<211> LENGTH: 6
<212> TYPE: PRT
<213> ORGANISM: Artificial Sequence
<220> FEATURE:
<223> OTHER INFORMATION: Synthetic peptide 57

<400> SEQUENCE: 59

Ser Pro Ser Ser Pro Ser
1               5

<210> SEQ ID NO 60
<211> LENGTH: 6
<212> TYPE: PRT
<213> ORGANISM: Artificial Sequence
<220> FEATURE:
<223> OTHER INFORMATION: Synthetic peptide 58

<400> SEQUENCE: 60

Ser Thr Pro Ser Thr Pro
1               5

<210> SEQ ID NO 61
<211> LENGTH: 6
```

```
<212> TYPE: PRT
<213> ORGANISM: Artificial Sequence
<220> FEATURE:
<223> OTHER INFORMATION: Synthetic peptide 59

<400> SEQUENCE: 61

Ser Thr Ser Ser Thr Ser
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic peptide 60

<400> SEQUENCE: 62

Pro Ser Ser Pro Ser Ser Pro Ser Ser
1               5

<210> SEQ ID NO 63
<211> LENGTH: 9
<212> TYPE: PRT
<213> ORGANISM: Artificial Sequence
<220> FEATURE:
<223> OTHER INFORMATION: Synthetic peptide 61

<400> SEQUENCE: 63

Pro Thr Pro Pro Thr Pro Pro Thr Pro
1               5

<210> SEQ ID NO 64
<211> LENGTH: 9
<212> TYPE: PRT
<213> ORGANISM: Artificial Sequence
<220> FEATURE:
<223> OTHER INFORMATION: Synthetic peptide 62

<400> SEQUENCE: 64

Pro Thr Ser Pro Thr Ser Pro Thr Ser
1               5

<210> SEQ ID NO 65
<211> LENGTH: 9
<212> TYPE: PRT
<213> ORGANISM: Artificial Sequence
<220> FEATURE:
<223> OTHER INFORMATION: Synthetic peptide 63

<400> SEQUENCE: 65

Ser Ser Pro Ser Ser Pro Ser Ser Pro
1               5

<210> SEQ ID NO 66
<211> LENGTH: 9
<212> TYPE: PRT
<213> ORGANISM: Artificial Sequence
<220> FEATURE:
<223> OTHER INFORMATION: Synthetic peptide 64

<400> SEQUENCE: 66

Ser Pro Ser Ser Pro Ser Ser Pro Ser
1               5

<210> SEQ ID NO 67
<211> LENGTH: 9
<212> TYPE: PRT
```

<213> ORGANISM: Artificial Sequence
<220> FEATURE:
<223> OTHER INFORMATION: Synthetic peptide 65

<400> SEQUENCE: 67

Ser Thr Pro Ser Thr Pro Ser Thr Pro
1               5

<210> SEQ ID NO 68
<211> LENGTH: 9
<212> TYPE: PRT
<213> ORGANISM: Artificial Sequence
<220> FEATURE:
<223> OTHER INFORMATION: Synthetic peptide 66

<400> SEQUENCE: 68

Ser Thr Ser Ser Thr Ser Ser Thr Ser
1               5

<210> SEQ ID NO 69
<211> LENGTH: 12
<212> TYPE: PRT
<213> ORGANISM: Artificial Sequence
<220> FEATURE:
<223> OTHER INFORMATION: Synthetic peptide 67

<400> SEQUENCE: 69

Pro Pro Ser Pro Pro Ser Pro Pro Ser Pro Pro Ser
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Synthetic peptide 68

<400> SEQUENCE: 70

Pro Pro Thr Pro Pro Thr Pro Pro Thr Pro Pro Thr
1               5                   10

<210> SEQ ID NO 71
<211> LENGTH: 12
<212> TYPE: PRT
<213> ORGANISM: Artificial Sequence
<220> FEATURE:
<223> OTHER INFORMATION: Synthetic peptide 69

<400> SEQUENCE: 71

Pro Pro Gln Pro Pro Gln Pro Pro Gln Pro Pro Gln
1               5                   10

<210> SEQ ID NO 72
<211> LENGTH: 15
<212> TYPE: PRT
<213> ORGANISM: Artificial Sequence
<220> FEATURE:
<223> OTHER INFORMATION: Synthetic peptide 70

<400> SEQUENCE: 72

Pro Ser Ser Pro Ser Ser Pro Ser Ser Pro Ser Ser Pro Ser Ser
1               5                   10                  15

<210> SEQ ID NO 73
<211> LENGTH: 15
<212> TYPE: PRT
<213> ORGANISM: Artificial Sequence
<220> FEATURE:
<223> OTHER INFORMATION: Synthetic peptide 71

<400> SEQUENCE: 73

Pro Thr Pro Pro Thr Pro Pro Thr Pro Pro Thr Pro Pro Thr Pro
1               5                   10                  15

<210> SEQ ID NO 74
<211> LENGTH: 15
<212> TYPE: PRT
<213> ORGANISM: Artificial Sequence
<220> FEATURE:
<223> OTHER INFORMATION: Synthetic peptide 72

<400> SEQUENCE: 74

Pro Thr Ser Pro Thr Ser Pro Thr Ser Pro Thr Ser Pro Thr Ser
1               5                   10                  15

<210> SEQ ID NO 75
<211> LENGTH: 15
<212> TYPE: PRT
<213> ORGANISM: Artificial Sequence
<220> FEATURE:
<223> OTHER INFORMATION: Synthetic peptide 73

<400> SEQUENCE: 75

Ser Ser Pro Ser Ser Pro Ser Ser Pro Ser Ser Pro Ser Ser Pro
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: Synthetic peptide 74

<400> SEQUENCE: 76

Ser Pro Ser Ser Pro Ser Ser Pro Ser Ser Pro Ser Ser Pro Ser
1               5                   10                  15

<210> SEQ ID NO 77
<211> LENGTH: 15
<212> TYPE: PRT
<213> ORGANISM: Artificial Sequence
<220> FEATURE:
<223> OTHER INFORMATION: Synthetic peptide 75

<400> SEQUENCE: 77

Ser Thr Pro Ser Thr Pro Ser Thr Pro Ser Thr Pro Ser Thr Pro
1               5                   10                  15

<210> SEQ ID NO 78
<211> LENGTH: 15
<212> TYPE: PRT
<213> ORGANISM: Artificial Sequence
<220> FEATURE:
<223> OTHER INFORMATION: Synthetic peptide 76

<400> SEQUENCE: 78

Ser Thr Ser Ser Thr Ser Ser Thr Ser Ser Thr Ser Ser Thr Ser
1               5                   10                  15

<210> SEQ ID NO 79
<211> LENGTH: 18
<212> TYPE: PRT
<213> ORGANISM: Artificial Sequence
<220> FEATURE:

<223> OTHER INFORMATION: Synthetic peptide 77

<400> SEQUENCE: 79

Pro Ser Ser Pro Ser Ser Pro Ser Ser Pro Ser Ser Pro Ser Ser Pro
1               5                   10                  15

Ser Ser

<210> SEQ ID NO 80
<211> LENGTH: 18
<212> TYPE: PRT
<213> ORGANISM: Artificial Sequence
<220> FEATURE:
<223> OTHER INFORMATION: Synthetic peptide 78

<400> SEQUENCE: 80

Pro Thr Pro Pro Thr Pro Pro Thr Pro Pro Thr Pro Pro Thr Pro Pro
1               5                   10                  15

Thr Pro

<210> SEQ ID NO 81
<211> LENGTH: 18
<212> TYPE: PRT
<213> ORGANISM: Artificial Sequence
<220> FEATURE:
<223> OTHER INFORMATION: Synthetic peptide 79

<400> SEQUENCE: 81

Pro Thr Ser Pro Thr Ser Pro Thr Ser Pro Thr Ser Pro Thr Ser Pro
1               5                   10                  15

Thr Ser

<210> SEQ ID NO 82
<211> LENGTH: 18
<212> TYPE: PRT
<213> ORGANISM: Artificial Sequence
<220> FEATURE:
<223> OTHER INFORMATION: Synthetic peptide 80

<400> SEQUENCE: 82

Ser Ser Pro Ser Ser Pro Ser Ser Pro Ser Ser Pro Ser Ser Pro Ser
1               5                   10                  15

Ser Pro

<210> SEQ ID NO 83
<211> LENGTH: 18
<212> TYPE: PRT
<213> ORGANISM: Artificial Sequence
<220> FEATURE:
<223> OTHER INFORMATION: Synthetic peptide 81

<400> SEQUENCE: 83

Ser Pro Ser Ser Pro Ser Ser Pro Ser Ser Pro Ser Ser Pro Ser Ser
1               5                   10                  15

Pro Ser

<210> SEQ ID NO 84
<211> LENGTH: 18
<212> TYPE: PRT
<213> ORGANISM: Artificial Sequence
<220> FEATURE:
<223> OTHER INFORMATION: Synthetic peptide 82

<400> SEQUENCE: 84

Ser Thr Pro Ser Thr Pro Ser Thr Pro Ser Thr Pro Ser Thr Pro Ser
1               5                   10                  15

Thr Pro

<210> SEQ ID NO 85
<211> LENGTH: 18
<212> TYPE: PRT
<213> ORGANISM: Artificial Sequence
<220> FEATURE:
<223> OTHER INFORMATION: Synthetic peptide 83

<400> SEQUENCE: 85

Ser Thr Ser Ser Thr Ser Ser Thr Ser Ser Thr Ser Ser Thr Ser Ser
1               5                   10                  15

Thr Ser

<210> SEQ ID NO 86
<211> LENGTH: 21
<212> TYPE: PRT
<213> ORGANISM: Artificial Sequence
<220> FEATURE:
<223> OTHER INFORMATION: Synthetic peptide 84

<400> SEQUENCE: 86

Pro Ser Ser Pro Ser Ser Pro Ser Ser Pro Ser Ser Pro Ser Ser Pro
1               5                   10                  15

Ser Ser Pro Ser Ser
            20

<210> SEQ ID NO 87
<211> LENGTH: 21
<212> TYPE: PRT
<213> ORGANISM: Artificial Sequence
<220> FEATURE:
<223> OTHER INFORMATION: Synthetic peptide 85

<400> SEQUENCE: 87

Pro Thr Pro Pro Thr Pro Pro Thr Pro Pro Thr Pro Pro Thr Pro Pro
1               5                   10                  15

Thr Pro Pro Thr Pro
            20

<210> SEQ ID NO 88
<211> LENGTH: 21
<212> TYPE: PRT
<213> ORGANISM: Artificial Sequence
<220> FEATURE:
<223> OTHER INFORMATION: Synthetic peptide 86

<400> SEQUENCE: 88

Pro Thr Ser Pro Thr Ser Pro Thr Ser Pro Thr Ser Pro Thr Ser Pro
1               5                   10                  15

Thr Ser Pro Thr Ser
            20

<210> SEQ ID NO 89
<211> LENGTH: 6
<212> TYPE: PRT
<213> ORGANISM: Artificial Sequence
<220> FEATURE:
<223> OTHER INFORMATION: Pep1

<400> SEQUENCE: 89

Pro Ser Ser Pro Ser Ser 1               5

<210> SEQ ID NO 90
<211> LENGTH: 6
<212> TYPE: PRT
<213> ORGANISM: Artificial Sequence
<220> FEATURE:
<223> OTHER INFORMATION: Pep2

<400> SEQUENCE: 90

Ser Ser Pro Ser Ser Pro
1               5

<210> SEQ ID NO 91
<211> LENGTH: 6
<212> TYPE: PRT
<213> ORGANISM: Artificial Sequence
<220> FEATURE:
<223> OTHER INFORMATION: Pep3

<400> SEQUENCE: 91

Pro Thr Pro Pro Thr Pro
1               5

<210> SEQ ID NO 92
<211> LENGTH: 6
<212> TYPE: PRT
<213> ORGANISM: Artificial Sequence
<220> FEATURE:
<223> OTHER INFORMATION: Pep4

<400> SEQUENCE: 92

Pro Thr Ser Pro Thr Ser
1               5

<210> SEQ ID NO 93
<211> LENGTH: 6
<212> TYPE: PRT
<213> ORGANISM: Artificial Sequence
<220> FEATURE:
<223> OTHER INFORMATION: Pep5

<400> SEQUENCE: 93

Ser Thr Pro Ser Thr Pro
1               5

<210> SEQ ID NO 94
<211> LENGTH: 6
<212> TYPE: PRT
<213> ORGANISM: Artificial Sequence
<220> FEATURE:
<223> OTHER INFORMATION: Pep6

<400> SEQUENCE: 94

Ser Thr Ser Ser Thr Ser
1               5

<210> SEQ ID NO 95
<211> LENGTH: 6
<212> TYPE: PRT
<213> ORGANISM: Artificial Sequence
<220> FEATURE:
<223> OTHER INFORMATION: Pep7

<400> SEQUENCE: 95

Ser Pro Ser Ser Pro Ser
1               5

```
<210> SEQ ID NO 96
<211> LENGTH: 6
<212> TYPE: PRT
<213> ORGANISM: Artificial Sequence
<220> FEATURE:
<223> OTHER INFORMATION: PEPTIDE2
<220> FEATURE:
<221> NAME/KEY: MISC_FEATURE
<222> LOCATION: (1)..(3)
<223> OTHER INFORMATION: Xaa is Proline, Serine, Threonine, Glutamine,
      Asparagine or Cysteine
<220> FEATURE:
<221> NAME/KEY: MISC_FEATURE
<222> LOCATION: (4)..(4)
<223> OTHER INFORMATION: Xaa is the same residue with the first Xaa
<220> FEATURE:
<221> NAME/KEY: MISC_FEATURE
<222> LOCATION: (5)..(5)
<223> OTHER INFORMATION: Xaa is the same residue with the second Xaa
<220> FEATURE:
<221> NAME/KEY: MISC_FEATURE
<222> LOCATION: (6)..(6)
<223> OTHER INFORMATION: Xaa is the same residue with the third Xaa

<400> SEQUENCE: 96

Xaa Xaa Xaa Xaa Xaa Xaa
1               5

<210> SEQ ID NO 97
<211> LENGTH: 9
<212> TYPE: PRT
<213> ORGANISM: Artificial Sequence
<220> FEATURE:
<223> OTHER INFORMATION: PEPTIDE3
<220> FEATURE:
<221> NAME/KEY: MISC_FEATURE
<222> LOCATION: (1)..(3)
<223> OTHER INFORMATION: Xaa is Proline, Serine, Threonine, Glutamine,
      Asparagine or Cysteine
<220> FEATURE:
<221> NAME/KEY: MISC_FEATURE
<222> LOCATION: (4)..(4)
<223> OTHER INFORMATION: Xaa is the same residue with the first Xaa
<220> FEATURE:
<221> NAME/KEY: MISC_FEATURE
<222> LOCATION: (5)..(5)
<223> OTHER INFORMATION: Xaa is the same residue with the second Xaa
<220> FEATURE:
<221> NAME/KEY: MISC_FEATURE
<222> LOCATION: (6)..(6)
<223> OTHER INFORMATION: Xaa is the same residue with the third Xaa
<220> FEATURE:
<221> NAME/KEY: MISC_FEATURE
<222> LOCATION: (7)..(7)
<223> OTHER INFORMATION: Xaa is the same residue with the first Xaa
<220> FEATURE:
<221> NAME/KEY: MISC_FEATURE
<222> LOCATION: (8)..(8)
<223> OTHER INFORMATION: Xaa is the same residue with the second Xaa
<220> FEATURE:
<221> NAME/KEY: MISC_FEATURE
<222> LOCATION: (9)..(9)
<223> OTHER INFORMATION: Xaa is the same residue with the third Xaa

<400> SEQUENCE: 97

Xaa Xaa Xaa Xaa Xaa Xaa Xaa Xaa Xaa
1               5

<210> SEQ ID NO 98
<211> LENGTH: 12
<212> TYPE: PRT
<213> ORGANISM: Artificial Sequence
<220> FEATURE:
```

```
<223> OTHER INFORMATION: PEPTIDE4
<220> FEATURE:
<221> NAME/KEY: MISC_FEATURE
<222> LOCATION: (1)..(3)
<223> OTHER INFORMATION: Xaa is Proline, Serine, Threonine, Glutamine,
      Asparagine or Cysteine
<220> FEATURE:
<221> NAME/KEY: MISC_FEATURE
<222> LOCATION: (4)..(4)
<223> OTHER INFORMATION: Xaa is the same residue with the first Xaa
<220> FEATURE:
<221> NAME/KEY: MISC_FEATURE
<222> LOCATION: (5)..(5)
<223> OTHER INFORMATION: Xaa is the same residue with the second Xaa
<220> FEATURE:
<221> NAME/KEY: MISC_FEATURE
<222> LOCATION: (6)..(6)
<223> OTHER INFORMATION: Xaa is the same residue with the third Xaa
<220> FEATURE:
<221> NAME/KEY: MISC_FEATURE
<222> LOCATION: (7)..(7)
<223> OTHER INFORMATION: Xaa is the same residue with the first Xaa
<220> FEATURE:
<221> NAME/KEY: MISC_FEATURE
<222> LOCATION: (8)..(8)
<223> OTHER INFORMATION: Xaa is the same residue with the second Xaa
<220> FEATURE:
<221> NAME/KEY: MISC_FEATURE
<222> LOCATION: (9)..(9)
<223> OTHER INFORMATION: Xaa is the same residue with the third Xaa
<220> FEATURE:
<221> NAME/KEY: MISC_FEATURE
<222> LOCATION: (10)..(10)
<223> OTHER INFORMATION: Xaa is the same residue with the first Xaa
<220> FEATURE:
<221> NAME/KEY: MISC_FEATURE
<222> LOCATION: (11)..(11)
<223> OTHER INFORMATION: Xaa is the same residue with the second Xaa
<220> FEATURE:
<221> NAME/KEY: MISC_FEATURE
<222> LOCATION: (12)..(12)
<223> OTHER INFORMATION: Xaa is the same residue with the third Xaa

<400> SEQUENCE: 98

Xaa Xaa Xaa Xaa Xaa Xaa Xaa Xaa Xaa Xaa Xaa Xaa
1               5                   10

<210> SEQ ID NO 99
<211> LENGTH: 15
<212> TYPE: PRT
<213> ORGANISM: Artificial Sequence
<220> FEATURE:
<223> OTHER INFORMATION: PEPTIDE5
<220> FEATURE:
<221> NAME/KEY: MISC_FEATURE
<222> LOCATION: (1)..(3)
<223> OTHER INFORMATION: Xaa is Proline, Serine, Threonine, Glutamine,
      Asparagine or Cysteine
<220> FEATURE:
<221> NAME/KEY: MISC_FEATURE
<222> LOCATION: (4)..(4)
<223> OTHER INFORMATION: Xaa is the same residue with the first Xaa
<220> FEATURE:
<221> NAME/KEY: MISC_FEATURE
<222> LOCATION: (5)..(5)
<223> OTHER INFORMATION: Xaa is the same residue with the second Xaa
<220> FEATURE:
<221> NAME/KEY: MISC_FEATURE
<222> LOCATION: (6)..(6)
<223> OTHER INFORMATION: Xaa is the same residue with the third Xaa
<220> FEATURE:
<221> NAME/KEY: MISC_FEATURE
<222> LOCATION: (7)..(7)
<223> OTHER INFORMATION: Xaa is the same residue with the first Xaa
<220> FEATURE:
<221> NAME/KEY: MISC_FEATURE
<222> LOCATION: (8)..(8)
```

```
<223> OTHER INFORMATION: Xaa is the same residue with the second Xaa
<220> FEATURE:
<221> NAME/KEY: MISC_FEATURE
<222> LOCATION: (9)..(9)
<223> OTHER INFORMATION: Xaa is the same residue with the third Xaa
<220> FEATURE:
<221> NAME/KEY: MISC_FEATURE
<222> LOCATION: (10)..(10)
<223> OTHER INFORMATION: Xaa is the same residue with the first Xaa
<220> FEATURE:
<221> NAME/KEY: MISC_FEATURE
<222> LOCATION: (11)..(11)
<223> OTHER INFORMATION: Xaa is the same residue with the second Xaa
<220> FEATURE:
<221> NAME/KEY: MISC_FEATURE
<222> LOCATION: (12)..(12)
<223> OTHER INFORMATION: Xaa is the same residue with the third Xaa
<220> FEATURE:
<221> NAME/KEY: MISC_FEATURE
<222> LOCATION: (13)..(13)
<223> OTHER INFORMATION: Xaa is the same residue with the first Xaa
<220> FEATURE:
<221> NAME/KEY: MISC_FEATURE
<222> LOCATION: (14)..(14)
<223> OTHER INFORMATION: Xaa is the same residue with the second Xaa
<220> FEATURE:
<221> NAME/KEY: MISC_FEATURE
<222> LOCATION: (15)..(15)
<223> OTHER INFORMATION: Xaa is the same residue with the third Xaa

<400> SEQUENCE: 99

Xaa Xaa Xaa Xaa Xaa Xaa Xaa Xaa Xaa Xaa Xaa Xaa Xaa Xaa Xaa
1               5                   10                  15

<210> SEQ ID NO 100
<211> LENGTH: 18
<212> TYPE: PRT
<213> ORGANISM: Artificial Sequence
<220> FEATURE:
<223> OTHER INFORMATION: PEPTIDE6
<220> FEATURE:
<221> NAME/KEY: MISC_FEATURE
<222> LOCATION: (1)..(3)
<223> OTHER INFORMATION: Xaa is Proline, Serine, Threonine, Glutamine,
      Asparagine or Cysteine
<220> FEATURE:
<221> NAME/KEY: MISC_FEATURE
<222> LOCATION: (4)..(4)
<223> OTHER INFORMATION: Xaa is the same residue with the first Xaa
<220> FEATURE:
<221> NAME/KEY: MISC_FEATURE
<222> LOCATION: (5)..(5)
<223> OTHER INFORMATION: Xaa is the same residue with the second Xaa
<220> FEATURE:
<221> NAME/KEY: MISC_FEATURE
<222> LOCATION: (6)..(6)
<223> OTHER INFORMATION: Xaa is the same residue with the third Xaa
<220> FEATURE:
<221> NAME/KEY: MISC_FEATURE
<222> LOCATION: (7)..(7)
<223> OTHER INFORMATION: Xaa is the same residue with the first Xaa
<220> FEATURE:
<221> NAME/KEY: MISC_FEATURE
<222> LOCATION: (8)..(8)
<223> OTHER INFORMATION: Xaa is the same residue with the second Xaa
<220> FEATURE:
<221> NAME/KEY: MISC_FEATURE
<222> LOCATION: (9)..(9)
<223> OTHER INFORMATION: Xaa is the same residue with the third Xaa
<220> FEATURE:
<221> NAME/KEY: MISC_FEATURE
<222> LOCATION: (10)..(10)
<223> OTHER INFORMATION: Xaa is the same residue with the first Xaa
<220> FEATURE:
<221> NAME/KEY: MISC_FEATURE
<222> LOCATION: (11)..(11)
<223> OTHER INFORMATION: Xaa is the same residue with the second Xaa
```

```
<220> FEATURE:
<221> NAME/KEY: MISC_FEATURE
<222> LOCATION: (12)..(12)
<223> OTHER INFORMATION: Xaa is the same residue with the third Xaa
<220> FEATURE:
<221> NAME/KEY: MISC_FEATURE
<222> LOCATION: (13)..(13)
<223> OTHER INFORMATION: Xaa is the same residue with the first Xaa
<220> FEATURE:
<221> NAME/KEY: MISC_FEATURE
<222> LOCATION: (14)..(14)
<223> OTHER INFORMATION: Xaa is the same residue with the second Xaa
<220> FEATURE:
<221> NAME/KEY: MISC_FEATURE
<222> LOCATION: (15)..(15)
<223> OTHER INFORMATION: Xaa is the same residue with the third Xaa
<220> FEATURE:
<221> NAME/KEY: MISC_FEATURE
<222> LOCATION: (16)..(16)
<223> OTHER INFORMATION: Xaa is the same residue with the first Xaa
<220> FEATURE:
<221> NAME/KEY: MISC_FEATURE
<222> LOCATION: (17)..(17)
<223> OTHER INFORMATION: Xaa is the same residue with the second Xaa
<220> FEATURE:
<221> NAME/KEY: MISC_FEATURE
<222> LOCATION: (18)..(18)
<223> OTHER INFORMATION: Xaa is the same residue with the third Xaa

<400> SEQUENCE: 100

Xaa Xaa Xaa Xaa Xaa Xaa Xaa Xaa Xaa Xaa Xaa Xaa Xaa Xaa Xaa Xaa
1               5                   10                  15

Xaa Xaa

<210> SEQ ID NO 101
<211> LENGTH: 21
<212> TYPE: PRT
<213> ORGANISM: Artificial Sequence
<220> FEATURE:
<223> OTHER INFORMATION: PEPTIDE7
<220> FEATURE:
<221> NAME/KEY: MISC_FEATURE
<222> LOCATION: (1)..(3)
<223> OTHER INFORMATION: Xaa is Proline, Serine, Threonine, Glutamine,
      Asparagine or Cysteine
<220> FEATURE:
<221> NAME/KEY: MISC_FEATURE
<222> LOCATION: (4)..(4)
<223> OTHER INFORMATION: Xaa is the same residue with the first Xaa
<220> FEATURE:
<221> NAME/KEY: MISC_FEATURE
<222> LOCATION: (5)..(5)
<223> OTHER INFORMATION: Xaa is the same residue with the second Xaa
<220> FEATURE:
<221> NAME/KEY: MISC_FEATURE
<222> LOCATION: (6)..(6)
<223> OTHER INFORMATION: Xaa is the same residue with the third Xaa
<220> FEATURE:
<221> NAME/KEY: MISC_FEATURE
<222> LOCATION: (7)..(7)
<223> OTHER INFORMATION: Xaa is the same residue with the first Xaa
<220> FEATURE:
<221> NAME/KEY: MISC_FEATURE
<222> LOCATION: (8)..(8)
<223> OTHER INFORMATION: Xaa is the same residue with the second Xaa
<220> FEATURE:
<221> NAME/KEY: MISC_FEATURE
<222> LOCATION: (9)..(9)
<223> OTHER INFORMATION: Xaa is the same residue with the third Xaa
<220> FEATURE:
<221> NAME/KEY: MISC_FEATURE
<222> LOCATION: (10)..(10)
<223> OTHER INFORMATION: Xaa is the same residue with the first Xaa
<220> FEATURE:
<221> NAME/KEY: MISC_FEATURE
<222> LOCATION: (11)..(11)
```

```
<223> OTHER INFORMATION: Xaa is the same residue with the second Xaa
<220> FEATURE:
<221> NAME/KEY: MISC_FEATURE
<222> LOCATION: (12)..(12)
<223> OTHER INFORMATION: Xaa is the same residue with the third Xaa
<220> FEATURE:
<221> NAME/KEY: MISC_FEATURE
<222> LOCATION: (13)..(13)
<223> OTHER INFORMATION: Xaa is the same residue with the first Xaa
<220> FEATURE:
<221> NAME/KEY: MISC_FEATURE
<222> LOCATION: (14)..(14)
<223> OTHER INFORMATION: Xaa is the same residue with the second Xaa
<220> FEATURE:
<221> NAME/KEY: MISC_FEATURE
<222> LOCATION: (15)..(15)
<223> OTHER INFORMATION: Xaa is the same residue with the third Xaa
<220> FEATURE:
<221> NAME/KEY: MISC_FEATURE
<222> LOCATION: (16)..(16)
<223> OTHER INFORMATION: Xaa is the same residue with the first Xaa
<220> FEATURE:
<221> NAME/KEY: MISC_FEATURE
<222> LOCATION: (17)..(17)
<223> OTHER INFORMATION: Xaa is the same residue with the second Xaa
<220> FEATURE:
<221> NAME/KEY: MISC_FEATURE
<222> LOCATION: (18)..(18)
<223> OTHER INFORMATION: Xaa is the same residue with the third Xaa
<220> FEATURE:
<221> NAME/KEY: MISC_FEATURE
<222> LOCATION: (19)..(19)
<223> OTHER INFORMATION: Xaa is the same residue with the first Xaa
<220> FEATURE:
<221> NAME/KEY: MISC_FEATURE
<222> LOCATION: (20)..(20)
<223> OTHER INFORMATION: Xaa is the same residue with the second Xaa
<220> FEATURE:
<221> NAME/KEY: MISC_FEATURE
<222> LOCATION: (21)..(21)
<223> OTHER INFORMATION: Xaa is the same residue with the third Xaa

<400> SEQUENCE: 101

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa
            20

<210> SEQ ID NO 102
<211> LENGTH: 24
<212> TYPE: PRT
<213> ORGANISM: Artificial Sequence
<220> FEATURE:
<223> OTHER INFORMATION: PEPTIDE8
<220> FEATURE:
<221> NAME/KEY: MISC_FEATURE
<222> LOCATION: (1)..(3)
<223> OTHER INFORMATION: Xaa is Proline, Serine, Threonine, Glutamine,
      Asparagine or Cysteine
<220> FEATURE:
<221> NAME/KEY: MISC_FEATURE
<222> LOCATION: (4)..(4)
<223> OTHER INFORMATION: Xaa is the same residue with the first Xaa
<220> FEATURE:
<221> NAME/KEY: MISC_FEATURE
<222> LOCATION: (5)..(5)
<223> OTHER INFORMATION: Xaa is the same residue with the second Xaa
<220> FEATURE:
<221> NAME/KEY: MISC_FEATURE
<222> LOCATION: (6)..(6)
<223> OTHER INFORMATION: Xaa is the same residue with the third Xaa
<220> FEATURE:
<221> NAME/KEY: MISC_FEATURE
<222> LOCATION: (7)..(7)
<223> OTHER INFORMATION: Xaa is the same residue with the first Xaa
<220> FEATURE:
```

```
<221> NAME/KEY: MISC_FEATURE
<222> LOCATION: (8)..(8)
<223> OTHER INFORMATION: Xaa is the same residue with the second Xaa
<220> FEATURE:
<221> NAME/KEY: MISC_FEATURE
<222> LOCATION: (9)..(9)
<223> OTHER INFORMATION: Xaa is the same residue with the third Xaa
<220> FEATURE:
<221> NAME/KEY: MISC_FEATURE
<222> LOCATION: (10)..(10)
<223> OTHER INFORMATION: Xaa is the same residue with the first Xaa
<220> FEATURE:
<221> NAME/KEY: MISC_FEATURE
<222> LOCATION: (11)..(11)
<223> OTHER INFORMATION: Xaa is the same residue with the second Xaa
<220> FEATURE:
<221> NAME/KEY: MISC_FEATURE
<222> LOCATION: (12)..(12)
<223> OTHER INFORMATION: Xaa is the same residue with the third Xaa
<220> FEATURE:
<221> NAME/KEY: MISC_FEATURE
<222> LOCATION: (13)..(13)
<223> OTHER INFORMATION: Xaa is the same residue with the first Xaa
<220> FEATURE:
<221> NAME/KEY: MISC_FEATURE
<222> LOCATION: (14)..(14)
<223> OTHER INFORMATION: Xaa is the same residue with the second Xaa
<220> FEATURE:
<221> NAME/KEY: MISC_FEATURE
<222> LOCATION: (15)..(15)
<223> OTHER INFORMATION: Xaa is the same residue with the third Xaa
<220> FEATURE:
<221> NAME/KEY: MISC_FEATURE
<222> LOCATION: (16)..(16)
<223> OTHER INFORMATION: Xaa is the same residue with the first Xaa
<220> FEATURE:
<221> NAME/KEY: MISC_FEATURE
<222> LOCATION: (17)..(17)
<223> OTHER INFORMATION: Xaa is the same residue with the second Xaa
<220> FEATURE:
<221> NAME/KEY: MISC_FEATURE
<222> LOCATION: (18)..(18)
<223> OTHER INFORMATION: Xaa is the same residue with the third Xaa
<220> FEATURE:
<221> NAME/KEY: MISC_FEATURE
<222> LOCATION: (19)..(19)
<223> OTHER INFORMATION: Xaa is the same residue with the first Xaa
<220> FEATURE:
<221> NAME/KEY: MISC_FEATURE
<222> LOCATION: (20)..(20)
<223> OTHER INFORMATION: Xaa is the same residue with the second Xaa
<220> FEATURE:
<221> NAME/KEY: MISC_FEATURE
<222> LOCATION: (21)..(21)
<223> OTHER INFORMATION: Xaa is the same residue with the third Xaa
<220> FEATURE:
<221> NAME/KEY: MISC_FEATURE
<222> LOCATION: (22)..(22)
<223> OTHER INFORMATION: Xaa is the same residue with the first Xaa
<220> FEATURE:
<221> NAME/KEY: MISC_FEATURE
<222> LOCATION: (23)..(23)
<223> OTHER INFORMATION: Xaa is the same residue with the second Xaa
<220> FEATURE:
<221> NAME/KEY: MISC_FEATURE
<222> LOCATION: (24)..(24)
<223> OTHER INFORMATION: Xaa is the same residue with the third Xaa

<400> SEQUENCE: 102

Xaa Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa
            20

<210> SEQ ID NO 103
<211> LENGTH: 27
```

```
<212> TYPE: PRT
<213> ORGANISM: Artificial Sequence
<220> FEATURE:
<223> OTHER INFORMATION: PEPTIDE9
<220> FEATURE:
<221> NAME/KEY: MISC_FEATURE
<222> LOCATION: (1)..(3)
<223> OTHER INFORMATION: Xaa is Proline, Serine, Threonine, Glutamine,
      Asparagine or Cysteine
<220> FEATURE:
<221> NAME/KEY: MISC_FEATURE
<222> LOCATION: (4)..(4)
<223> OTHER INFORMATION: Xaa is the same residue with the first Xaa
<220> FEATURE:
<221> NAME/KEY: MISC_FEATURE
<222> LOCATION: (5)..(5)
<223> OTHER INFORMATION: Xaa is the same residue with the second Xaa
<220> FEATURE:
<221> NAME/KEY: MISC_FEATURE
<222> LOCATION: (6)..(6)
<223> OTHER INFORMATION: Xaa is the same residue with the third Xaa
<220> FEATURE:
<221> NAME/KEY: MISC_FEATURE
<222> LOCATION: (7)..(7)
<223> OTHER INFORMATION: Xaa is the same residue with the first Xaa
<220> FEATURE:
<221> NAME/KEY: MISC_FEATURE
<222> LOCATION: (8)..(8)
<223> OTHER INFORMATION: Xaa is the same residue with the second Xaa
<220> FEATURE:
<221> NAME/KEY: MISC_FEATURE
<222> LOCATION: (9)..(9)
<223> OTHER INFORMATION: Xaa is the same residue with the third Xaa
<220> FEATURE:
<221> NAME/KEY: MISC_FEATURE
<222> LOCATION: (10)..(10)
<223> OTHER INFORMATION: Xaa is the same residue with the first Xaa
<220> FEATURE:
<221> NAME/KEY: MISC_FEATURE
<222> LOCATION: (11)..(11)
<223> OTHER INFORMATION: Xaa is the same residue with the second Xaa
<220> FEATURE:
<221> NAME/KEY: MISC_FEATURE
<222> LOCATION: (12)..(12)
<223> OTHER INFORMATION: Xaa is the same residue with the third Xaa
<220> FEATURE:
<221> NAME/KEY: MISC_FEATURE
<222> LOCATION: (13)..(13)
<223> OTHER INFORMATION: Xaa is the same residue with the first Xaa
<220> FEATURE:
<221> NAME/KEY: MISC_FEATURE
<222> LOCATION: (14)..(14)
<223> OTHER INFORMATION: Xaa is the same residue with the second Xaa
<220> FEATURE:
<221> NAME/KEY: MISC_FEATURE
<222> LOCATION: (15)..(15)
<223> OTHER INFORMATION: Xaa is the same residue with the third Xaa
<220> FEATURE:
<221> NAME/KEY: MISC_FEATURE
<222> LOCATION: (16)..(16)
<223> OTHER INFORMATION: Xaa is the same residue with the first Xaa
<220> FEATURE:
<221> NAME/KEY: MISC_FEATURE
<222> LOCATION: (17)..(17)
<223> OTHER INFORMATION: Xaa is the same residue with the second Xaa
<220> FEATURE:
<221> NAME/KEY: MISC_FEATURE
<222> LOCATION: (18)..(18)
<223> OTHER INFORMATION: Xaa is the same residue with the third Xaa
<220> FEATURE:
<221> NAME/KEY: MISC_FEATURE
<222> LOCATION: (19)..(19)
<223> OTHER INFORMATION: Xaa is the same residue with the first Xaa
<220> FEATURE:
<221> NAME/KEY: MISC_FEATURE
<222> LOCATION: (20)..(20)
<223> OTHER INFORMATION: Xaa is the same residue with the second Xaa
<220> FEATURE:
<221> NAME/KEY: MISC_FEATURE
```

```
<222> LOCATION: (21)..(21)
<223> OTHER INFORMATION: Xaa is the same residue with the third Xaa
<220> FEATURE:
<221> NAME/KEY: MISC_FEATURE
<222> LOCATION: (22)..(22)
<223> OTHER INFORMATION: Xaa is the same residue with the first Xaa
<220> FEATURE:
<221> NAME/KEY: MISC_FEATURE
<222> LOCATION: (23)..(23)
<223> OTHER INFORMATION: Xaa is the same residue with the second Xaa
<220> FEATURE:
<221> NAME/KEY: MISC_FEATURE
<222> LOCATION: (24)..(24)
<223> OTHER INFORMATION: Xaa is the same residue with the third Xaa
<220> FEATURE:
<221> NAME/KEY: MISC_FEATURE
<222> LOCATION: (25)..(25)
<223> OTHER INFORMATION: Xaa is the same residue with the first Xaa
<220> FEATURE:
<221> NAME/KEY: MISC_FEATURE
<222> LOCATION: (26)..(26)
<223> OTHER INFORMATION: Xaa is the same residue with the second Xaa
<220> FEATURE:
<221> NAME/KEY: MISC_FEATURE
<222> LOCATION: (27)..(27)
<223> OTHER INFORMATION: Xaa is the same residue with the third Xaa

<400> SEQUENCE: 103

Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa
            20                  25

<210> SEQ ID NO 104
<211> LENGTH: 30
<212> TYPE: PRT
<213> ORGANISM: Artificial Sequence
<220> FEATURE:
<223> OTHER INFORMATION: PEPTIDE10
<220> FEATURE:
<221> NAME/KEY: MISC_FEATURE
<222> LOCATION: (1)..(3)
<223> OTHER INFORMATION: Xaa is Proline, Serine, Threonine, Glutamine,
      Asparagine or Cysteine
<220> FEATURE:
<221> NAME/KEY: MISC_FEATURE
<222> LOCATION: (4)..(4)
<223> OTHER INFORMATION: Xaa is the same residue with the first Xaa
<220> FEATURE:
<221> NAME/KEY: MISC_FEATURE
<222> LOCATION: (5)..(5)
<223> OTHER INFORMATION: Xaa is the same residue with the second Xaa
<220> FEATURE:
<221> NAME/KEY: MISC_FEATURE
<222> LOCATION: (6)..(6)
<223> OTHER INFORMATION: Xaa is the same residue with the third Xaa
<220> FEATURE:
<221> NAME/KEY: MISC_FEATURE
<222> LOCATION: (7)..(7)
<223> OTHER INFORMATION: Xaa is the same residue with the first Xaa
<220> FEATURE:
<221> NAME/KEY: MISC_FEATURE
<222> LOCATION: (8)..(8)
<223> OTHER INFORMATION: Xaa is the same residue with the second Xaa
<220> FEATURE:
<221> NAME/KEY: MISC_FEATURE
<222> LOCATION: (9)..(9)
<223> OTHER INFORMATION: Xaa is the same residue with the third Xaa
<220> FEATURE:
<221> NAME/KEY: MISC_FEATURE
<222> LOCATION: (10)..(10)
<223> OTHER INFORMATION: Xaa is the same residue with the first Xaa
<220> FEATURE:
<221> NAME/KEY: MISC_FEATURE
<222> LOCATION: (11)..(11)
<223> OTHER INFORMATION: Xaa is the same residue with the second Xaa
```

```
<220> FEATURE:
<221> NAME/KEY: MISC_FEATURE
<222> LOCATION: (12)..(12)
<223> OTHER INFORMATION: Xaa is the same residue with the third Xaa
<220> FEATURE:
<221> NAME/KEY: MISC_FEATURE
<222> LOCATION: (13)..(13)
<223> OTHER INFORMATION: Xaa is the same residue with the first Xaa
<220> FEATURE:
<221> NAME/KEY: MISC_FEATURE
<222> LOCATION: (14)..(14)
<223> OTHER INFORMATION: Xaa is the same residue with the second Xaa
<220> FEATURE:
<221> NAME/KEY: MISC_FEATURE
<222> LOCATION: (15)..(15)
<223> OTHER INFORMATION: Xaa is the same residue with the third Xaa
<220> FEATURE:
<221> NAME/KEY: MISC_FEATURE
<222> LOCATION: (16)..(16)
<223> OTHER INFORMATION: Xaa is the same residue with the first Xaa
<220> FEATURE:
<221> NAME/KEY: MISC_FEATURE
<222> LOCATION: (17)..(17)
<223> OTHER INFORMATION: Xaa is the same residue with the second Xaa
<220> FEATURE:
<221> NAME/KEY: MISC_FEATURE
<222> LOCATION: (18)..(18)
<223> OTHER INFORMATION: Xaa is the same residue with the third Xaa
<220> FEATURE:
<221> NAME/KEY: MISC_FEATURE
<222> LOCATION: (19)..(19)
<223> OTHER INFORMATION: Xaa is the same residue with the first Xaa
<220> FEATURE:
<221> NAME/KEY: MISC_FEATURE
<222> LOCATION: (20)..(20)
<223> OTHER INFORMATION: Xaa is the same residue with the second Xaa
<220> FEATURE:
<221> NAME/KEY: MISC_FEATURE
<222> LOCATION: (21)..(21)
<223> OTHER INFORMATION: Xaa is the same residue with the third Xaa
<220> FEATURE:
<221> NAME/KEY: MISC_FEATURE
<222> LOCATION: (22)..(22)
<223> OTHER INFORMATION: Xaa is the same residue with the first Xaa
<220> FEATURE:
<221> NAME/KEY: MISC_FEATURE
<222> LOCATION: (23)..(23)
<223> OTHER INFORMATION: Xaa is the same residue with the second Xaa
<220> FEATURE:
<221> NAME/KEY: MISC_FEATURE
<222> LOCATION: (24)..(24)
<223> OTHER INFORMATION: Xaa is the same residue with the third Xaa
<220> FEATURE:
<221> NAME/KEY: MISC_FEATURE
<222> LOCATION: (25)..(25)
<223> OTHER INFORMATION: Xaa is the same residue with the first Xaa
<220> FEATURE:
<221> NAME/KEY: MISC_FEATURE
<222> LOCATION: (26)..(26)
<223> OTHER INFORMATION: Xaa is the same residue with the second Xaa
<220> FEATURE:
<221> NAME/KEY: MISC_FEATURE
<222> LOCATION: (27)..(27)
<223> OTHER INFORMATION: Xaa is the same residue with the third Xaa
<220> FEATURE:
<221> NAME/KEY: MISC_FEATURE
<222> LOCATION: (28)..(28)
<223> OTHER INFORMATION: Xaa is the same residue with the first Xaa
<220> FEATURE:
<221> NAME/KEY: MISC_FEATURE
<222> LOCATION: (29)..(29)
<223> OTHER INFORMATION: Xaa is the same residue with the second Xaa
<220> FEATURE:
<221> NAME/KEY: MISC_FEATURE
<222> LOCATION: (30)..(30)
<223> OTHER INFORMATION: Xaa is the same residue with the third Xaa

<400> SEQUENCE: 104
```

```
Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Xaa Xaa Xaa Xaa Xaa Xaa
            20                  25                  30

<210> SEQ ID NO 105
<211> LENGTH: 6
<212> TYPE: PRT
<213> ORGANISM: Artificial Sequence
<220> FEATURE:
<223> OTHER INFORMATION: PSP2

<400> SEQUENCE: 105

Pro Ser Pro Pro Ser Pro
1               5

<210> SEQ ID NO 106
<211> LENGTH: 9
<212> TYPE: PRT
<213> ORGANISM: Artificial Sequence
<220> FEATURE:
<223> OTHER INFORMATION: PSP3

<400> SEQUENCE: 106

Pro Ser Pro Pro Ser Pro Pro Ser Pro
1               5
```

USE OF PEPTIDES AS THERAPEUTIC AGENT FOR AUTOIMMUNE DISEASES AND BONE DISEASES

This application is a National Phase of International Application No. PCT/KR2018/010873 filed on 14 Sep. 2018, which is claims priority of Korean Patent Application No. 10-2017-0118947 filed on Sep. 15, 2017; Korean Patent Application No. 10-2017-0118949 filed on Sep. 15, 2017; Korean Patent Application No. 10-2018-0110473 filed on Sep. 14, 2018; and Korean Patent Application No. 10-2018-0110480 filed on Sep. 14, 2018, which is hereby incorporated herein by reference in its entirety for all purposes.

TECHNICAL FIELD

The present invention relates to use of peptides as a therapeutic agent for bone disease or autoimmune disease and more particularly, to a peptide consisting of an amino acid sequence represented by Formula 1 of the present invention, and use of the peptide for treating bone disease including osteoporosis, inflammatory disease, or autoimmune diseases including rheumatoid arthritis.

BACKGROUND ART

Bone tissue consists of extracellular substances such as collagen and glycoprotein, and various kinds of cells such as osteoblasts, osteoclasts, and osteocytes. Particularly, the mutual balance of osteoblasts and osteoclasts is essential for the formation of a healthy skeletal system. In other words, bone metabolism and bone remodeling are important for balanced activity between the osteoblasts that form a bone matrix and the osteoclasts that resorb the bone to maintain the homeostasis of the bone.

The bone tissue consists of extracellular substances such as collagen and glycoprotein, and various kinds of cells such as osteoblasts, osteoclasts, and osteocytes. Further, the bone tissue is a metabolic organ where bone resorption by osteoclasts and new bone matrix formation and mineralization by osteoblasts repeatedly occur, and the bone formation by the activity of osteoblasts is greater than bone resorption by the activity of osteoclasts. The bone remodeling is a process of removing old bone after growth and replacing the removed bone with new bone, and hormones such as parathyroid hormone (PTH), calcitonin, and estrogen, various growth factors secreted from the bone tissue such as insulin-like growth factor I (IGFI), and cytokines such as tumor necrosis factor-α (TNF-α) regulate the activity balance of osteoblasts and osteoclasts and maintain homeostasis. When the balance of these osteoblasts and osteoclasts is broken, diseases such as osteoporosis or arthritis are induced.

In particular, when the balance of osteoblasts and osteoclasts is broken, excessive bone destruction is caused by the osteoclasts, leading to diseases such as osteoporosis. The osteoclasts as cells specialized for the resorption of bone during the bone metabolism are formed through a differentiation program from monocytes or macrophages as progenitor cells. Further, since the osteoclasts secrete various collagenases and proteases to cause the bone resorption while binding to bone through αvβ3 integrin and the like and preparing an acidic environment, suppression of these osteoclasts may be an effective method of treating bone diseases.

In addition, autoimmune diseases cause abnormalities of a human immune system so that self-cells attack self-cells. The human immune system basically recognizes microorganisms invaded to the human body and generation of cancer cells as external antigens and has a strong power to attack and remove the recognized microorganisms and cancer cells, but does not attack its own cells due to self-tolerance. This is called a self-tolerance phenomenon of the human body. However, when the self-tolerance of the immune system is destroyed, the human body activates autoreactive T cells in response to self-cells (or autoantigens) and generates autoantibodies to constantly destroy self-cells and cause inflammation and immune responses.

Cells that specifically respond to antigens in the immune system include T cells and B cells. When the T cells meet a specific antigen presented by an antigen presenting cell, the T cells respond according to the antigen. When the antigen presented by the antigen presenting cell is recognized as 'non-self', an immune response to remove the antigen is shown, and when the antigen is recognized as 'self', tolerance in which the immune response is ignored is shown. When the T cells are activated against antigens, most B cells are successively activated and B cells are converted into plasma cells to produce antibodies that specifically respond to the recognized specific antigen. Therefore, when tolerance is broken in the human body and autoimmunity occurs, the T cells recognize and activate autoantigens abnormally, the B cells are activated to produce autoantibodies that respond to autoantigens, and then an immune response to attack self-cells occurs in the body.

Similarly, even in organ transplant patients, when the immune system recognizes the transplanted tissue as 'non-self' after organ transplantation, organ transplant rejection reaction occurs to attack and remove the transplanted organ. In order to suppress the organ transplant rejection reaction, various immunosuppressants have been used, such as suppressing the activation of immune cells and inhibiting the migration of immune cells to transplanted organs, but the continuous use of immunosuppressants causes various side-effects.

Meanwhile, recently, it has been found that Th17 cells as a CD4$^+$ T cell system play a key role in the inflammatory induction and progression of autoimmune diseases, and the importance of these Th17 cells is further increasing by finding that the IL-17 secreted from these cells is directly associated with autoimmune diseases.

In addition, the Th17 cells are known to induce RANKL and various inflammatory cytokines, which are the major causes of bone destruction (Chabaud and Miossec, 2001; Connell and McInnes, 2006), to further activate inflammation and joint destruction mechanisms. Therefore, since the Th17 cells are recognized as key pathogens in signaling processes related to autoimmune diseases including rheumatoid arthritis and bone diseases, the discovery of candidates that effectively inhibit Th17 cell differentiation has been required.

Further, rheumatoid arthritis is an inflammatory disease characterized by polyarthritis, and an autoimmune phenomenon is known as a main mechanism. In the symptom, while inflammation of the articular synovial membrane tissue occurs, macrophages, dendritic cells, T lymphocytes, B lymphocytes, and the like migrate to the synovial membrane tissue, and as a result, a joint fluid is increased and thus the joint is swollen to cause pain. As this inflammation continues, an inflammatory synovial membrane tissue causes hyperplasia to destroy the bone and cartilage, thus a joint structure is modified and movement disorders occur. In addition, according to results of various studies, it has been known that in patients with rheumatoid arthritis, inflammatory cytokines produce collagenase and neutral protease in synovial membrane fibroblasts and chondrocytes, and these produced enzymes destroy collagen and proteoglycans to destroy the articular cartilage.

Therefore, the present inventors have made efforts to develop a new therapeutic agent for bone disease and autoimmune disease with an effective therapeutic effect while minimizing side-effects as a therapeutic agent. As a result, the present inventors found that the peptides prepared in the present invention may be usefully used for the treatment of bone disease including osteoporosis, inflammatory disease, or autoimmune disease including rheumatoid arthritis and completed the present invention.

SUMMARY OF INVENTION

Technical Problem

An object of the present invention is to provide peptides for preventing or treating bone disease, inflammatory disease, and autoimmune disease.

Solution to Problem

In order to achieve the object, the present invention provides a peptide consisting of an amino acid sequence of Formula 1 represented by SEQ ID NO: 1 below, and a pharmaceutical composition for preventing and treating bone disease, inflammatory disease or autoimmune disease or health foods for preventing and improving bone disease, inflammatory disease or autoimmune disease, containing the peptide as an active ingredient.

$$(X_1—X_2—X_3)_n \quad \text{[Formula 1]}$$

Wherein, $X_1$ to $X_3$ each is any one selected from the group consisting of proline (P), serine (S), threonine (T), glutamine (Q), asparagine (N), and cysteine (C), n is an integer from 1 to 10, and the case where the amino acid sequence of Formula 1 above includes a PSP represented by SEQ ID NO: 2 and n=1 to 3 is excluded.

Advantageous Effects of Invention

According to the present invention, it has been confirmed that the peptides of the present invention significantly inhibit the activity of T cells and the differentiation of T helper 17 cells (Th17 cells), which are associated with autoimmune disease, and have remarkable effects of treating and improving arthritis in an arthritis animal model. Therefore, the peptides may be used as an active ingredient in therapeutic agents for bone disease, inflammatory disease or various autoimmune diseases such as rheumatoid arthritis.

DESCRIPTION OF EMBODIMENTS

Figure 1:
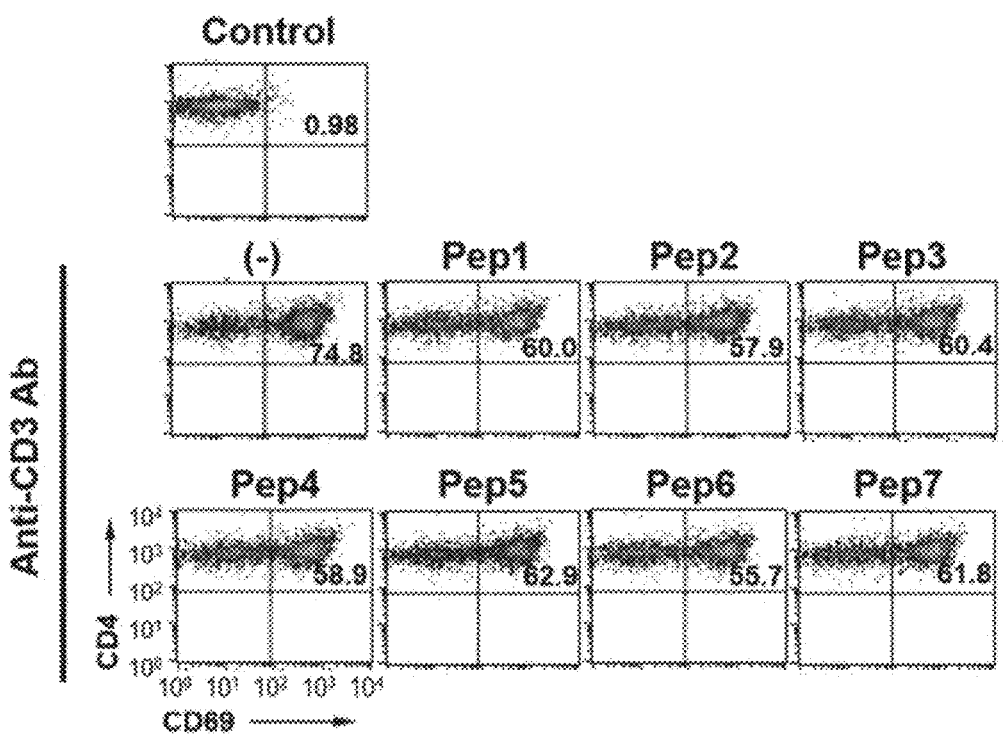
FIG. 1 is a diagram showing an active T cell population (%) by a synthetic peptide of the present invention.

Hereinafter, terms of the present invention will be defined as follows.

In the present invention, general one-letter or three-letter codes for naturally existing amino acids are used, and three-letter codes generally allowed for other amino acids, such as α-aminoisobutyric acid (Aib) and N-methylglycine (Sar) are also used. The amino acids mentioned herein as abbreviations are described according to the IUPAC-IUB nomenclature.

The "peptide" of the present invention refers to a polymer consisting of two or more amino acids linked by an amide bond (or peptide bond), and for the purposes of the present invention, refers to a peptide having a therapeutic effect on bone disease, inflammatory disease, and autoimmune disease.

The "stability" of the present invention means not only in-vivo stability that protects the peptides of the present invention from the attack of protein cleavage enzymes in vivo, but also storage stability (e.g., room-temperature storage stability).

The "prevention" of the present invention means all actions that inhibit disease or delay the onset of the disease by administration of a pharmaceutical composition according to the present invention.

The "treatment" of the present invention means all actions that improve or advantageously change symptoms of the disease by the administration of the pharmaceutical composition according to the present invention.

The "subject" of the present invention refers to a subject in need of treatment for diseases, and more particularly, refers to mammals such as human or non-human primates, mice, dogs, cats, horses and cattle.

The "improvement" of the present invention means all actions that at least reduce parameters associated with conditions to be treated, e.g., the degree of symptoms.

Hereinafter, the present invention will be described in more detail.

The present invention provides a peptide consisting of an amino acid sequence of Formula 1 represented by SEQ ID NO: 1 below and a pharmaceutical composition for preventing and treating bone disease, inflammatory disease, or autoimmune disease containing the peptide as an active ingredient:

$$(X_1—X_2—X_3)_n \quad \text{[Formula 1]}$$

wherein, $X_1$ to $X_3$ each is any one selected from the group consisting of proline (P), serine (S), threonine (T), glutamine (Q), asparagine (N), and cysteine (C), n is an integer from 1 to 10, and the case where the amino acid sequence of Formula 1 above includes a PSP represented by SEQ ID NO: 2 and n=1 to 3 is excluded.

The peptide may be prepared as various peptides using Formula 1 above, which are all included in the present invention. In addition, the $X_1$ to $X_3$ each is preferably any one selected from the group consisting of proline (P), serine (S), and threonine (T), and more preferably proline (P) or serine (S), but the present invention is not limited thereto.

In addition, in Formula above, n is preferably an integer of 1 to 6, and more preferably an integer of 1 to 3.

The peptide of the present invention may be obtained by various methods well-known in the art. As an example, the peptide may be prepared by using polynucleotide recombination and a protein expression system or prepared by in-vitro synthesis through chemical synthesis such as peptide synthesis, cell-free protein synthesis, and the like.

In addition, in order to obtain better chemical stability, enhanced pharmacological properties (half-life, absorbency, titer, efficacy, etc.), modified specificity (e.g., a wide biological activity spectrum), and reduced antigenicity, a protective group may bind to an N- or C-terminus of the peptide. Preferably, the protective group may be an acetyl group, a fluorenylmethoxy carbonyl group, a formyl group, a palmitoyl group, a myristyl group, a stearyl group, or polyethylene glycol (PEG), but may include any ingredient that may enhance the modification of the peptide, particularly the stability of the peptide, without limitation.

The bone disease is preferably at least one selected from the group consisting of arthritis, osteoporosis, bone metastatic cancer, solid cancer bone metastasis, musculoskeletal complications due to solid cancer bone metastasis, hypercalcemia caused by malignant tumor, multiple myeloma, primary bone tumor, periodontal disease, inflammatory alveolar bone resorption disease, inflammatory bone resorption disease, and Paget's disease, but is not limited thereto.

The inflammatory disease is preferably selected from the group consisting of atopy, psoriasis, dermatitis, allergies, arthritis, rhinitis, otitis media, sore throat, tonsillitis, cystitis, nephritis, pelvic inflammatory, Crohn's disease, ulcerative colitis, ankylosing spondylitis, systemic lupus erythematodes (SLE), asthma, edema, delayed allergy (Type IV allergy), transplant rejection, graft-versus-host disease, autoimmune encephalomyelitis, multiple sclerosis, inflammatory bowel disease, cystic fibrosis, diabetic retinopathy, ischemic-reperfusion injury, vascular restenosis, glomerulonephritis, and gastrointestinal allergy, but is not limited thereto.

The autoimmune disease is preferably selected from the group consisting of rheumatoid arthritis, Sjogren's syndrome, systemic sclerosis, polymyositis, systemic angitis, mixed connective tissue disease, Crohn's disease, Hashimoto's disease, Grave's disease, Goodpasture's syndrome, Guillain-Barre syndrome, idiopathic thrombocytopenic purpura, irritable bowel syndrome, myasthenia gravis, narcolepsy, vulgaris ulcer, pernicious anemia, primary biliary cirrhosis, ulcerative colitis, vasculitis, Wegener's granulomatosis, and psoriasis, but is not limited thereto.

In addition, since the same therapeutic effect may be exhibited even by using polynucleotides encoding the peptide of the present invention, it is obvious that the polynucleotides encoding the peptide of the present invention are also included in the present invention.

In a specific embodiment of the present invention, the present inventors prepared various peptides using Formula 1 above [$(X_1-X_2-X_3)_n$] (see Table 1).

Figure 2:
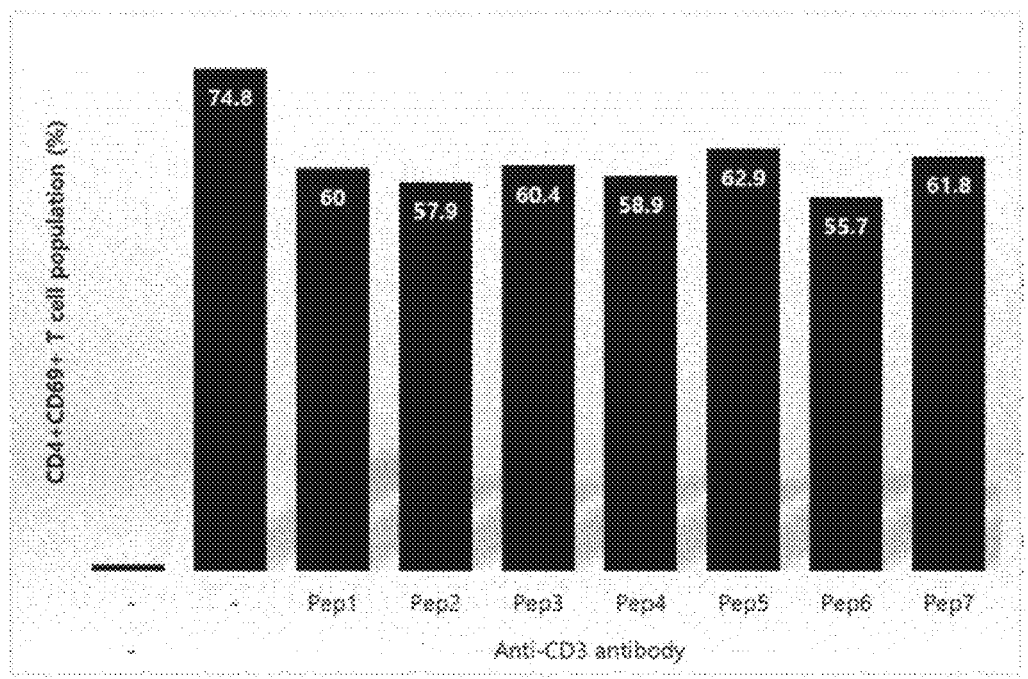
FIG. 2 is a diagram showing an active T cell population (%) by a synthetic peptide of the present invention in a graph.
Figure 3:
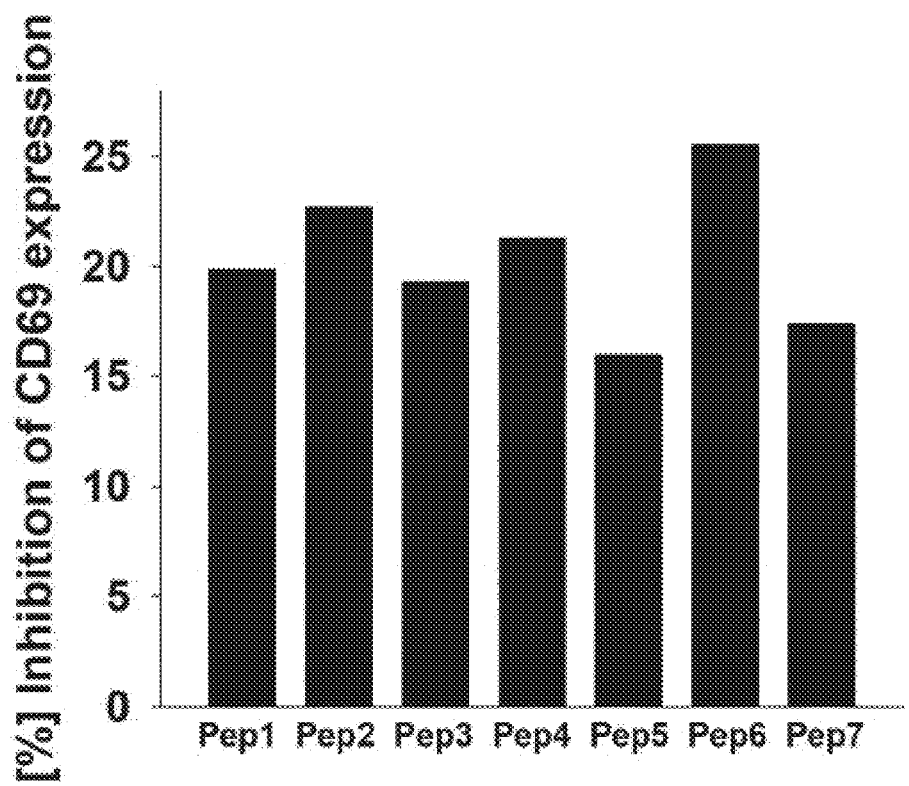
FIG. 3 is a diagram showing a T cell activation inhibition rate (%) by a synthetic peptide of the present invention.

In addition, the present inventors confirmed a T cell activity inhibitory effect of the peptides, and as a result, the peptides of Table 1 significantly inhibit the T cell activity by an average of 15% to 25%, and the T cell activity inhibitory effect of peptides randomly selected among the peptides was shown in FIGS. 1 and 3 (see FIGS. 1 to 3).

Figure 4:
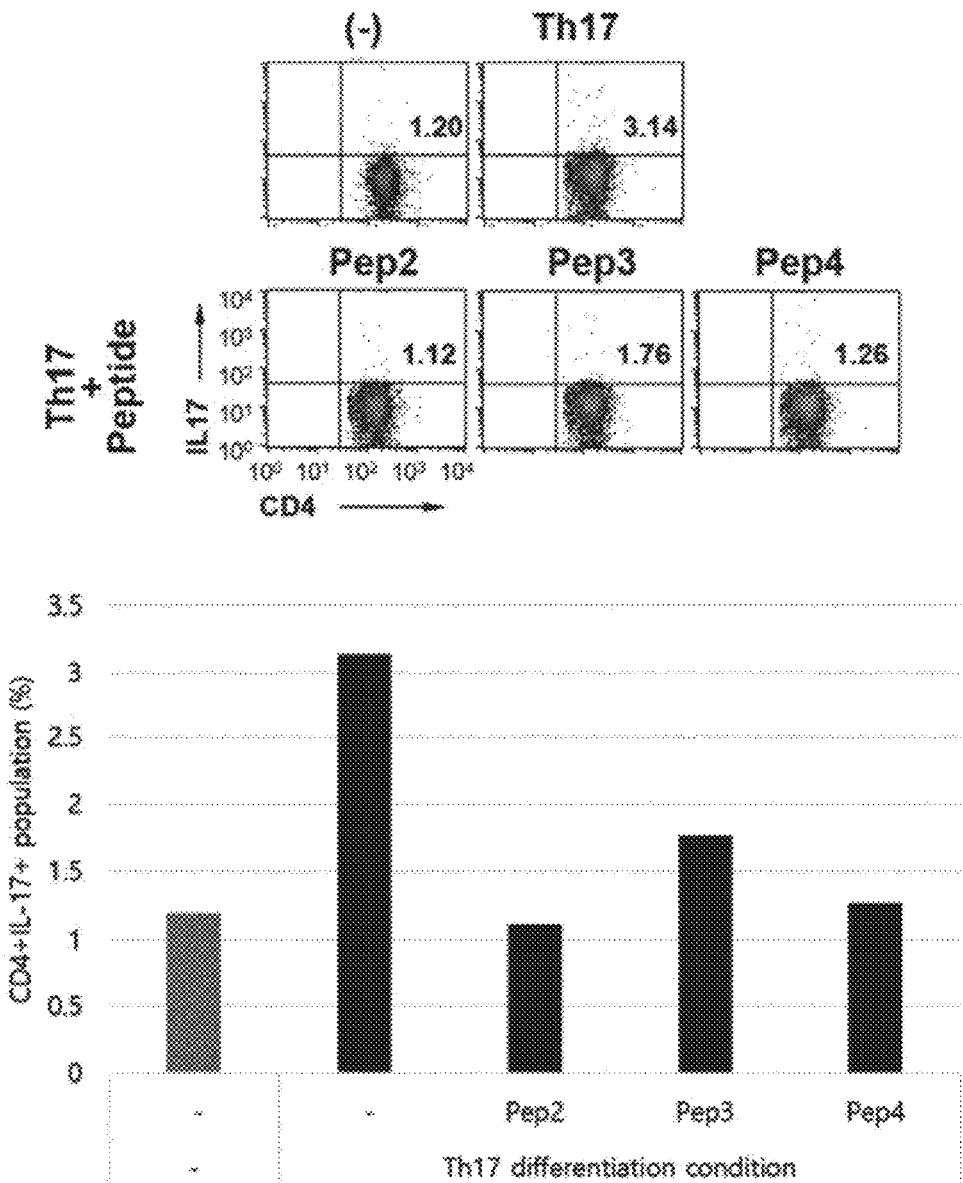
FIG. 4 is a diagram showing a Th17 cell differentiation inhibitory effect by a synthetic peptide of the present invention.

In addition, the present inventors confirmed that a synthetic peptide prepared in Example 1 inhibits Th17 cell differentiation, and as a result, confirmed that the peptides of the present invention significantly inhibit the Th17 cell differentiation (see FIG. 4).

Further, the present inventors prepared a rheumatoid arthritis animal model (see FIG. 5) and then confirmed a therapeutic effect of the peptides of the present invention, and as a result, confirmed that the peptides showed a significant arthritis improvement effect, particularly, a similar effect compared to a positive control group MTX (see FIGS. 6 to 9).

Therefore, since it has been confirmed that the peptides of the present invention significantly inhibit the activity of T cells and the differentiation of T helper 17 cells (Th17 cells), which are associated with autoimmune diseases, and have remarkable effects of treating and improving arthritis in an arthritis animal model, the peptides may be used as an active ingredient in therapeutic agents for bone disease, inflammatory disease or various autoimmune diseases such as rheumatoid arthritis.

On the other hand, the peptides of the present invention or polynucleotides encoding the same may be carried in pharmaceutically acceptable carriers such as colloidal suspensions, powders, saline, lipids, liposomes, microspheres, or nano spherical particles. These peptides or polynucleotides may form a complex with a vehicle or be associated with the vehicle and may be carried in vivo by using vehicle systems known in the art, such as lipids, liposomes, microparticles, gold, nanoparticles, polymers, condensation reagents, polysaccharides, polyamino acids, dendrimers, saponins, adsorption enhancing substances or fatty acids.

Besides, the pharmaceutically acceptable carrier may include lactose, dextrose, sucrose, sorbitol, mannitol, starch, acacia, rubber, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, and mineral oil, which are generally used in preparation, but is not limited thereto. Further, the pharmaceutical composition may further include a lubricant, a wetting agent, a sweetening agent, a flavoring agent, an emulsifying agent, a suspending agent, a preservative, and the like, in addition to the ingredients.

The pharmaceutical composition of the present invention may be administered orally or parenterally (e.g., applied intramuscularly, intravenously, intraperitoneally, subcutaneously, intradermally, or topically) according to a desired method, and a dose thereof varies depending on the condition and weight of a patient, a degree of disease, a drug form, and route and time of administration, but may be appropriately selected by those skilled in the art.

The pharmaceutical composition of the present invention is administered in a pharmaceutically effective dose. In the present invention, the "pharmaceutically effective dose" refers to an amount sufficient to treat the diseases at a reasonable benefit/risk ratio applicable to medical treatment, and an effective dose level may be determined according to elements including the type and severity of disease of a patient, activity of a drug, sensitivity to a drug, a time of administration, a route of administration and an emission rate, duration of treatment, and simultaneously used drugs, and other elements well-known in the medical field. The pharmaceutical composition according to the present invention may be administered as an individual therapeutic agent or in combination with other therapeutic agents for bone disease, inflammatory disease, or autoimmune disease, and administered simultaneously, separately, or sequentially with conventional therapeutic agents for bone disease, inflammatory disease, or autoimmune disease, and may be administered singly or multiply. It is important to administer an amount capable of obtaining a maximum effect with a minimal amount without side-effects by considering all the elements, and this may be easily determined by those skilled in the art.

Specifically, the effective dose of the pharmaceutical composition of the present invention may vary depending on the age, sex, condition, and weight of a patient, absorbance of an active ingredient in vivo, an inactivation rate, an excretion rate, a disease type, and drugs to be used in combination, and may be increased or decreased according to a route of administration, the severity of obesity, sex, weight, age, and the like.

Further, the present invention provides health foods for preventing and improving bone disease, inflammatory disease or autoimmune disease containing the peptide of the present invention or polynucleotides encoding the same as an active ingredient.

The health foods may be used simultaneously or separately with a drug for treatment before or after the onset of the corresponding disease in order to prevent or improve the disease.

In the health foods of the present invention, the active ingredient may be added to the foods as it is or used with other foods or food ingredients, and may be appropriately used according to a general method. The mixing amount of the active ingredients may be suitably determined according to the purpose of use thereof (prevention or improvement). In general, in preparation of foods or beverages, the composition of the present invention may be added preferably in an amount of 15 wt % or less, more preferably 10 wt % or less with respect to raw materials. However, in the case of long-term ingestion for the purpose of health and hygiene or health regulation, the amount may be used below the above range.

The health foods of the present invention may contain other ingredients as essential ingredients without particular limitation, in addition to the active ingredients. For example, like general beverages, various flavoring agents or natural carbohydrates may be contained as an additional ingredient. Examples of the above-mentioned natural carbohydrates may include monosaccharides, such as glucose, fructose, and the like; disaccharides, such as maltose, sucrose, and the like; and general sugars, such as polysaccharides such as dextrin, cyclodextrin, and the like, and sugar alcohols such as xylitol, sorbitol, erythritol. In addition to those described above, as the flavoring agent, natural flavoring agents (thaumatin, *stevia* extracts (e.g., rebaudioside A, glycyrrhizin, etc.)) and synthetic flavoring agents (saccharin, aspartame, etc.) may be advantageously used. The ratio of the natural carbohydrates may be appropriately determined by the selection of those skilled in the art.

In addition, the health foods of the present invention may contain various nutrients, vitamins, minerals (electrolytes), flavoring agents such as synthetic and natural flavoring agents, coloring agents and enhancers (cheese, chocolate, etc.), pectic acid and salts thereof, alginic acid and salts thereof, organic acid, a protective colloidal thickener, a pH adjusting agent, a stabilizer, a preservative, glycerin, alcohol, a carbonic acid agent used in a carbonated drink, and the like. These ingredients may be used independently or in combination, and the ratio of these additives may also be appropriately selected by those skilled in the art.

Hereinafter, the present invention will be described in detail by Examples and Test Examples.

However, the following Examples and Test Examples are just illustrative of the present invention, and the contents of the present invention are not limited to the following Examples and Test Examples.

<Example 1> Preparation of Peptides

Various peptides were prepared based on the following Formula 1. Subsequently, each of the synthesized peptides was purified and separated using high performance liquid chromatography (SHIMADZU Prominence HPLC), and a column used is a Shiseido capcell pak C18 column (4.6×50 mm). In addition, the mass of each synthesized peptide was confirmed by using a mass spectrometer (HP 1100 series LC/MSD).

$$(X_1-X_2-X_3)_n \qquad [\text{Formula 1}]$$

wherein, $X_1$ to $X_3$ each is any one selected from the group consisting of proline (P), serine (S), threonine (T), glutamine (Q), asparagine (N), and cysteine (C), n is an integer from 1 to 10, and the case where the amino acid sequence of Formula 1 above includes a PSP represented by SEQ ID NO: 2 and n=1 to 3 is excluded.

In addition, the peptides synthesized by the method were listed in Table 1 below.

TABLE 1

| No. | Synthetic peptide | SEQ ID NO: |
|---|---|---|
| 1 | PPS | 3 |
| 2 | PPT | 4 |
| 3 | PPQ | 5 |
| 4 | PPN | 6 |
| 5 | PSS | 7 |
| 6 | PST | 8 |
| 7 | PSQ | 9 |
| 8 | PSN | 10 |
| 9 | PSC | 11 |
| 10 | PTP | 12 |
| 11 | PTS | 13 |
| 12 | PTT | 14 |
| 13 | PTQ | 15 |
| 14 | PTN | 16 |
| 15 | PTC | 17 |
| 16 | PQP | 18 |
| 17 | PQS | 19 |
| 18 | PQT | 20 |
| 19 | PQN | 21 |
| 20 | PQC | 22 |

TABLE 1-continued

| No. | Synthetic peptide | SEQ ID NO: |
|---|---|---|
| 21 | PNP | 23 |
| 22 | PNS | 24 |
| 23 | PNT | 25 |
| 24 | PNQ | 26 |
| 25 | PNN | 27 |
| 26 | PNC | 28 |
| 27 | PCP | 29 |
| 28 | PCS | 30 |
| 29 | PCT | 31 |
| 30 | PCQ | 32 |
| 31 | PCN | 33 |
| 32 | PCC | 34 |
| 33 | SSP | 35 |
| 34 | SPS | 36 |
| 35 | SPT | 37 |
| 36 | SPQ | 38 |
| 37 | SPN | 39 |
| 38 | STP | 40 |
| 39 | STS | 41 |
| 40 | TPP | 42 |
| 41 | TPS | 43 |
| 42 | TSP | 44 |
| 43 | TSS | 45 |
| 44 | PPSPPS | 46 |
| 45 | PPTPPT | 47 |
| 46 | PPQPPQ | 48 |
| 47 | PPNPPN | 49 |
| 48 | PSSPSS | 50 |
| 49 | PSTPST | 51 |
| 50 | PSQPSQ | 52 |
| 51 | PSNPSN | 53 |
| 52 | PSCPSC | 54 |
| 53 | PTPPTP | 55 |
| 54 | PTSPTS | 56 |
| 55 | PTTPTT | 57 |
| 56 | SSPSSP | 58 |
| 57 | SPSSPS | 59 |
| 58 | STPSTP | 60 |
| 59 | STSSTS | 61 |

TABLE 1-continued

| No. | Synthetic peptide | SEQ ID NO: |
|---|---|---|
| 60 | PSSPSSPSS | 62 |
| 61 | PTPPTPPTP | 63 |
| 62 | PTSPTSPTS | 64 |
| 63 | SSPSSPSSP | 65 |
| 64 | SPSSPSSPS | 66 |
| 65 | STPSTPSTP | 67 |
| 66 | STSSTSSTS | 68 |
| 67 | PPSPPSPPSPPS | 69 |
| 68 | PPTPPTPPTPPT | 70 |
| 69 | PPQPPQPPQPPQ | 71 |
| 70 | PSSPSSPSSPSS | 72 |
| 71 | PTPPTPPTPPTP | 73 |
| 72 | PTSPTSPTSPTS | 74 |
| 73 | SSPSSPSSPSSP | 75 |
| 74 | SPSSPSSPSSPS | 76 |
| 75 | STPSTPSTPSTP | 77 |
| 76 | STSSTSSTSSTS | 78 |
| 77 | PSSPSSPSSPSSPSS | 79 |
| 78 | PTPPTPPTPPTPPTP | 80 |
| 79 | PTSPTSPTSPTSPTS | 81 |
| 80 | SSPSSPSSPSSPSSP | 82 |
| 81 | SPSSPSSPSSPSSPS | 83 |
| 82 | STPSTPSTPSTPSTP | 84 |
| 83 | STSSTSSTSSTSSTS | 85 |
| 84 | PSSPSSPSSPSSPSSPSS | 86 |
| 85 | PTPPTPPTPPTPPTPPTP | 87 |
| 86 | PTSPTSPTSPTSPTSPTS | 88 |

<Test Example 1> Confirmation of T Cell Activity Inhibitory Effect

In order to confirm the T cell activity inhibitory effect of the synthetic peptide prepared in Example 1, an ex vivo activity inhibition test was performed using T cells extracted from the lymph nodes of a mouse.

Specifically, at first, in order to induce activation of T cells, CD3 antibodies were coated on a 96 well plate and incubated overnight at 4° C. to prepare 96 wells attached with the CD3 antibodies. Thereafter, naive T cells extracted from the mouse were seeded in the 96 well plate by $1 \times 10^5$/well, treated with each of the synthetic peptides prepared in Example 1 and incubated for 18 hours, and then the population of the active T cells was confirmed by flow cytometry. To this end, the same number of cells were collected from each incubated group and washed with PBS, and then the collected cells were subjected to staining by using rabbit anti-mouse CD4 as a helper T cell marker and a rabbit anti-mouse CD69 antibody as a T-cell activation marker. The cells were washed with PBS and then CD4+ CD69+ T cell population was analyzed.

As a result, it was confirmed that the peptides synthesized in Example 1 significantly inhibited T cell activity by an average of 15% to 25%.

In addition, among the peptides synthesized in Example 1, the T cell activity inhibitory effect of the peptides shown in Table 2 was shown in FIGS. 1 to 3.

Specifically, it was confirmed that compared to a group that did not induce activation (0.98%), active T cells increased by 74.8% in a group activated with the CD3 antibody, and decreased by 55% to 62% in a group treated with each synthetic peptide. In addition, it was confirmed that the active T cell inhibition rate of each synthetic peptide was about 15% up to 25%, similarly to the peptides synthesized in Example 1.

Therefore, it was confirmed that the synthetic peptides of the present invention may be used to treat autoimmune diseases by significantly inhibiting the T cell activity (FIGS. 1 to 3).

TABLE 2

| Name of peptide | Amino acid sequence | SEQ ID NO: |
|---|---|---|
| Pep1 | PSSPSS | 89 |
| Pep2 | SSPSSP | 90 |
| Pep3 | PTPPTP | 91 |
| Pep4 | PTSPTS | 92 |
| Pep5 | STPSTP | 93 |
| Pep6 | STSSTS | 94 |
| Pep7 | SPSSPS | 95 |

<Test Example 2> Confirmation of Th 17 Cell Differentiation Inhibitory Effect

In order to confirm the efficacy of the synthetic peptides prepared in Example 1 to inhibit Th17 cell differentiation, naive $CD4^+$ T cells extracted from lymph nodes of the mouse were treated with IL-6 20 ng/ml and TGF-beta 5 ng/ml together with TCR activation to induce differentiation into Th17 cells.

At the same time, three peptides Pep2, Pep3, and Pep4 disclosed in Table 2 of Test Example 1 were treated at a concentration of 10 ng/ml to 1000 ng/ml, respectively. Then, after incubation for 3 days, CD4+IL-17+ T cell population was analyzed.

As a result, as shown in FIG. 4, there was a tendency of about 2.5-fold increase in a group that induced Th17 differentiation (3.14%), compared to a group that did not induce differentiation into Th17 cells (1.2%), and in a group treated with peptides Pep2, Pep3, and Pep4, it was confirmed that a ratio of Th17 cells was reduced similarly to the group that did not induce differentiation (FIG. 3).

Figure 5:
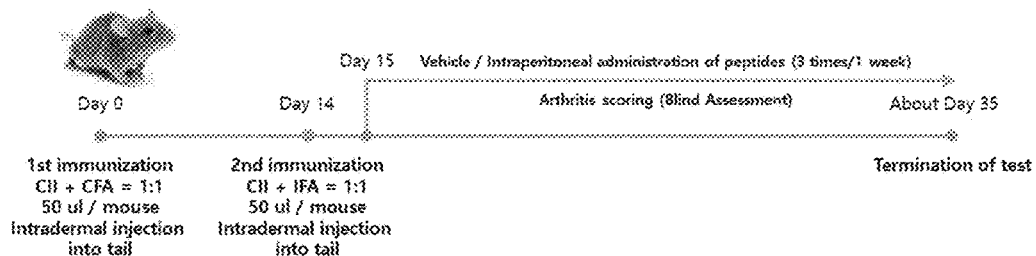
FIG. 5 is a schematic diagram schematically showing a process of preparing a collagen-induced arthritis mouse model and a time of administration of peptides according to the present invention.
Figure 6:
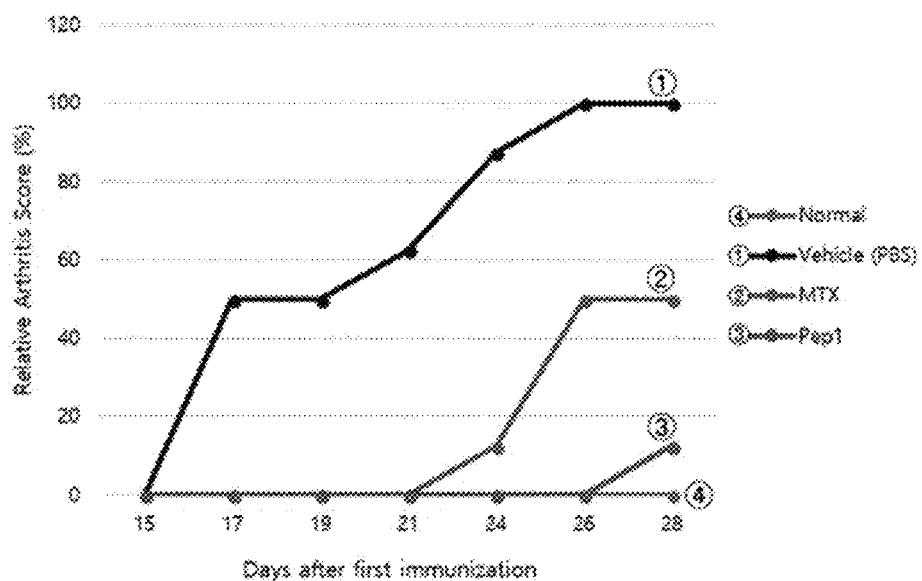
FIG. 6 is a diagram showing an arthritis improvement effect of a peptide Pep1 of the present invention.
Figure 6:
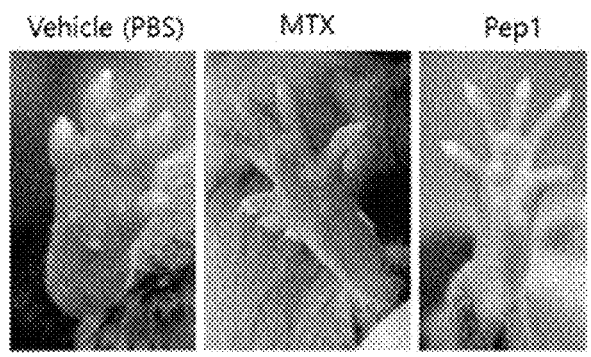
Figure 7:
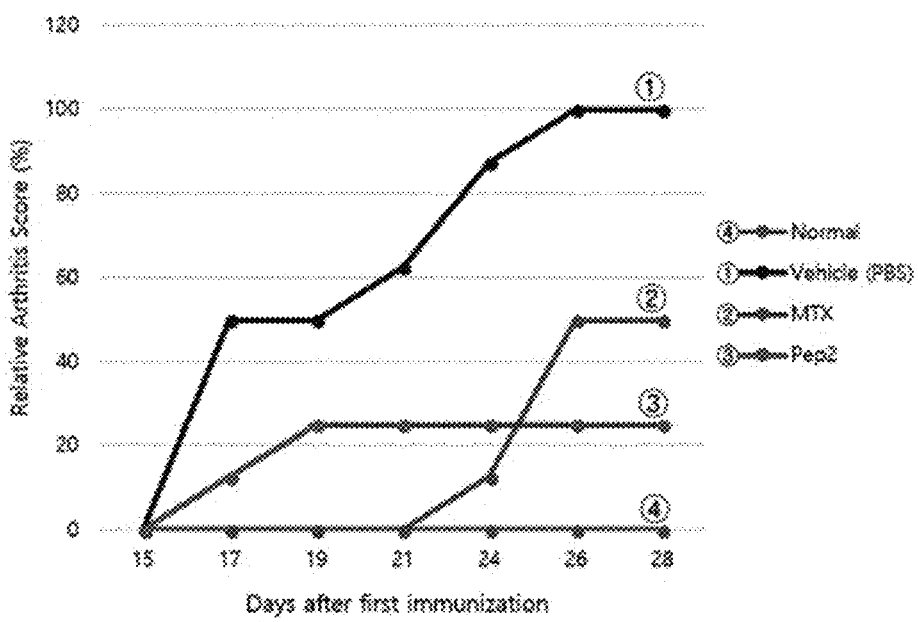
FIG. 7 is a diagram showing an arthritis improvement effect of a peptide Pep2 of the present invention.
Figure 7:
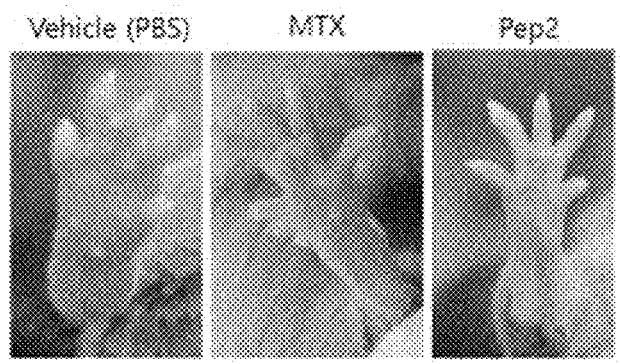
Figure 8:
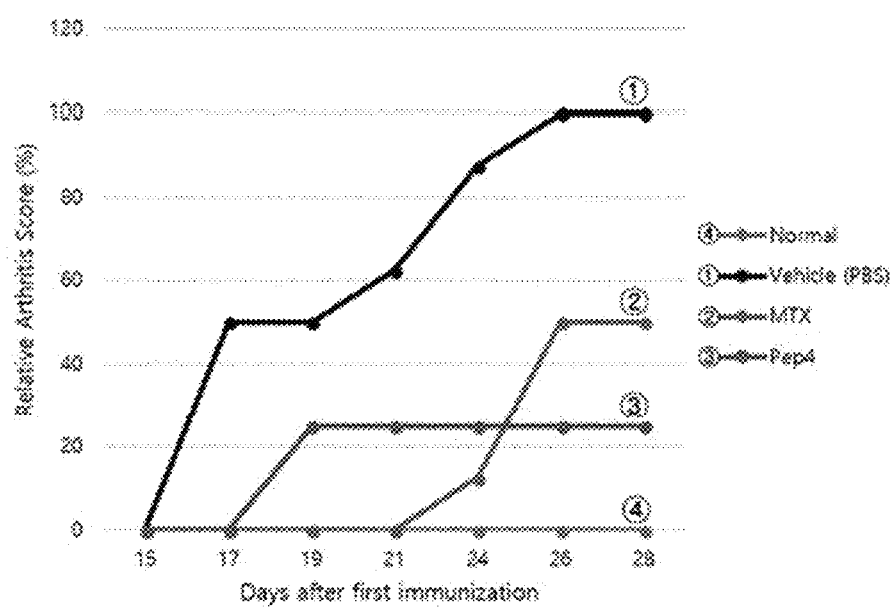
FIG. 8 is a diagram showing an arthritis improvement effect of a peptide Pep4 of the present invention.
Figure 8:
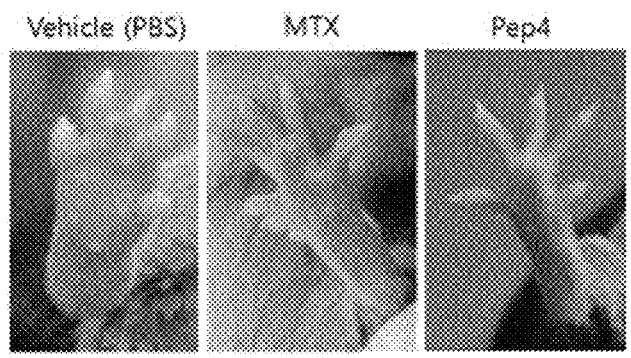
Figure 9:
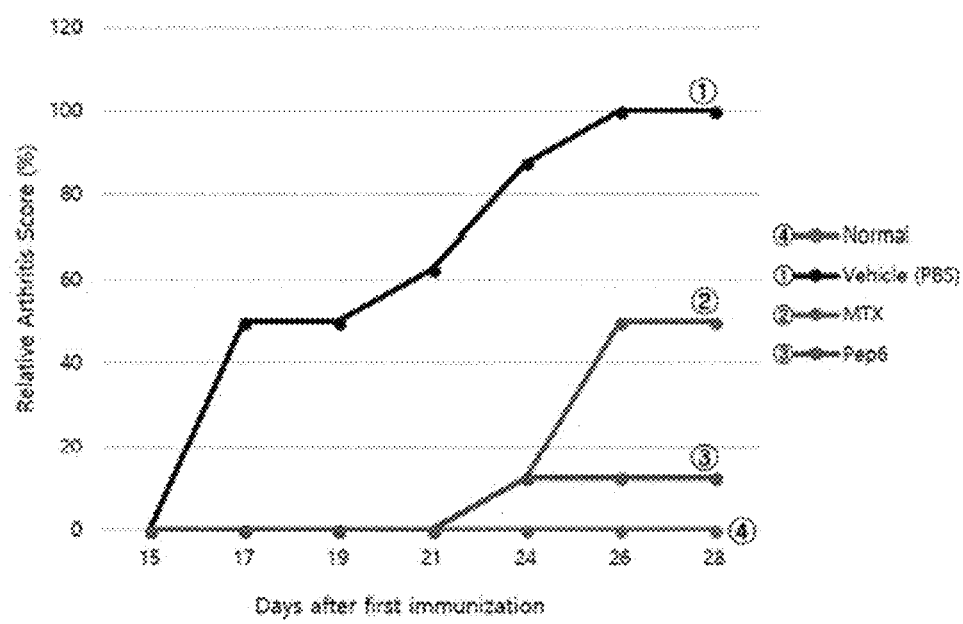
FIG. 9 is a diagram showing an arthritis improvement effect of a peptide Pep6 of the present invention.
Figure 9:
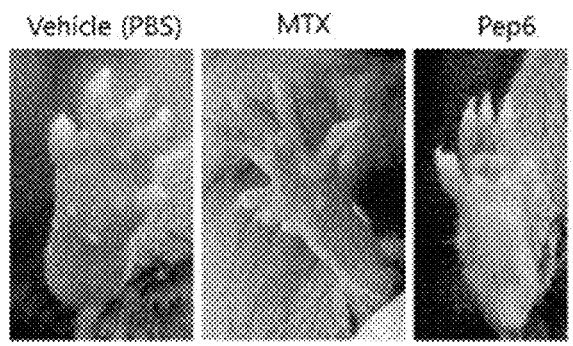

<Test Example 3> Confirmation of Rheumatoid Arthritis Treatment Effect Using Collagen-Induced Arthritis (CIA) Mouse Model <3-1> Preparation of Rheumatoid Arthritis Mouse Model In order to confirm a rheumatoid arthritis improvement effect of the peptides prepared in Example 1, a rheumatoid arthritis mouse model was prepared with reference to a known literature (Nat Protoc. 2007; 2 (5):

Specifically, a CIA mouse model is a mouse model most commonly used in a rheumatoid arthritis animal test as an autoimmune disease arthritis model having characteristics similar to human rheumatoid arthritis. In the CIA mouse model, bovine type II collagen (Chondrex, USA) was mixed and emulsified with a Freund's complete adjuvant (Chondrex, USA) at 1:1, and then first immunization was performed by injecting 50 µl of the emulsified collagen solution intradermally into a 6-week-old DBA/1J mouse tail. On 2 weeks after the first immunization, bovine type II collagen was mixed and emulsified with a Freund's incomplete adjuvant (Chondrex, USA) at 1:1, and then second immunization (boosting) was performed by injecting 50 µl of the emulsified collagen solution induced) intradermally into the mouse tail. After the second immunization, each peptide was intraperitoneally administered 3 times a week from the following day to observe a therapeutic effect of the peptides for rheumatoid arthritis. The administered peptides were selected as four peptides Pep1, Pep2, Pep4, and Pep6 shown in Table 2 (FIG. 5).

<3-2> Confirmation of Treatment Effect Using Rheumatoid Arthritis Mouse Model

In order to examine the progression of rheumatoid arthritis according to the peptide treatment of the present invention, the severity of rheumatoid arthritis over time was evaluated and measured by a rheumatoid arthritis progress index.

Two observers, who did not know specific test conditions, evaluated the progression of arthritis three times a week. At this time, the arthritis progress index was evaluated as Points 0 to 4 per leg in accordance with the arthritis progress evaluation criteria by Rossoliniec, etc. in Table 2 below and shown to total Points 0 to 16 (sum of four legs). Thereafter, an average value of the results evaluated by the two observers was calculated to quantify the severity of arthritis.

TABLE 3

| Score | Symptoms |
|---|---|
| Point 0 | There was no edema or swelling |
| Point 1 | Mild edema and redness confined to the foot or ankle joint were observed. |
| Point 2 | Mild swelling and redness across the tarsal bone at the ankle joint were observed. |
| Point 3 | Moderate swelling and redness across the tarsal bone at the ankle joint were observed. |
| Point 4 | There were edema and redness throughout the leg from the ankle, and joint stiffness was observed. |

As a result, as shown in FIGS. 6 to 9, it can be seen that arthritis scores are significantly increased in CIA-induced mice (Vehicle control; PBS) as compared to a normal mouse group, and it was confirmed that the efficacy of arthritis improvement was shown in a group intraperitoneally administered with four peptides Pep1, Pep2, Pep4, and Pep6, respectively. In addition, it was confirmed that the similar efficacy was shown compared to the positive control group MTX (FIGS. 6 to 9).

Therefore, it was confirmed that the peptides of the present invention may be used as therapeutic agents for various bone diseases including arthritis and autoimmune diseases.

The invention claimed is:

1. A synthetic peptide consisting of an amino acid sequence of Formula 1 below:

$$(X_1—X_2—X_3)_n$$ [Formula 1]

wherein, $X_1$ and $X_2$ are serine (S), to $X_3$ is proline (P),
n is an integer from 2 to 10,
when n is 2, the amino acid sequence of Formula 1 is represented by SEQ ID NO: 96,
when n is 3, the amino acid sequence of Formula 1 is represented by SEQ ID NO: 97,
when n is 4, the amino acid sequence of Formula 1 is represented by SEQ ID NO: 98,
when n is 5, the amino acid sequence of Formula 1 is represented by SEQ ID NO: 99,
when n is 6, the amino acid sequence of Formula 1 is represented by SEQ ID NO: 100,
when n is 7, the amino acid sequence of Formula 1 is represented by SEQ ID NO: 101,
when n is 8, the amino acid sequence of Formula 1 is represented by SEQ ID NO: 102,
when n is 9, the amino acid sequence of Formula 1 is represented by SEQ ID NO: 103,
when n is 10, the amino acid sequence of Formula 1 is represented by SEQ ID NO: 104.

2. The synthetic peptide according to claim 1, wherein an N- or C terminus of the peptide is bound to a protective group selected from the group consisting of an acetyl group, a fluorenylmethoxycarbonyl group, a formyl group, a palmitoyl group, a myristyl group, a stearyl group, and polyethylene glycol (PEG).

3. A method for treating bone disease, inflammatory disease or autoimmune disease, comprising administering a synthetic peptide consisting of an amino acid sequence of Formula 1 below in a pharmaceutically effective dose to a subject with bone disease, inflammatory disease or autoimmune disease:

$$(X_1—X_2—X_3)_n$$ [Formula 1]

wherein, $X_1$ and $X_2$ are serine (S), $X_3$ is proline (P),
n is an integer from 2 to 10,
when n is 2, the amino acid sequence of Formula 1 is represented by SEQ ID NO: 96,
when n is 3, the amino acid sequence of Formula 1 is represented by SEQ ID NO: 97,
when n is 4, the amino acid sequence of Formula 1 is represented by SEQ ID NO: 98,
when n is 5, the amino acid sequence of Formula 1 is represented by SEQ ID NO: 99,
when n is 6, the amino acid sequence of Formula 1 is represented by SEQ ID NO: 100,
when n is 7, the amino acid sequence of Formula 1 is represented by SEQ ID NO: 101,
when n is 8, the amino acid sequence of Formula 1 is represented by SEQ ID NO: 102,
when n is 9, the amino acid sequence of Formula 1 is represented by SEQ ID NO: 103,
when n is 10, the amino acid sequence of Formula 1 is represented by SEQ ID NO: 104.

4. The method according to claim 3, wherein the bone disease is at least one selected from the group consisting of arthritis, osteoporosis, bone metastatic cancer, solid cancer bone metastasis, musculoskeletal complications due to solid cancer bone metastasis, hypercalcemia caused by malignant tumor, multiple myeloma, primary bone tumor, periodontal disease, inflammatory alveolar bone disease, inflammatory bone resorption disease, and Paget's disease.

5. The method according to claim 3, wherein the inflammatory disease is selected from the group consisting of atopy, psoriasis, dermatitis, allergies, arthritis, rhinitis, otitis media, sore throat, tonsillitis, cystitis, nephritis, pelvic inflammatory, Crohn's disease, ulcerative colitis, ankylosing spondylitis, systemic lupus erythematodes (SLE), asthma, edema, delayed allergy (Type IV allergy), transplant rejection, graft-versus-host disease, autoimmune encephalomyelitis, multiple sclerosis, inflammatory bowel disease, cystic fibrosis, diabetic retinopathy, ischemic-reperfusion injury, vascular restenosis, glomerulonephritis, and gastrointestinal allergy.

6. The method according to claim 3, wherein the autoimmune disease is selected from the group consisting of rheumatoid arthritis, Sjogren's syndrome, systemic sclerosis, polymyositis, systemic angitis, mixed connective tissue disease, Crohn's disease, Hashimoto's disease, Grave's disease, Goodpasture's syndrome, Guillain-Barre syndrome, idiopathic thrombocytopenic purpura, irritable bowel syndrome, myasthenia gravis, narcolepsy, vulgaris ulcer, pernicious anemia, primary biliary cirrhosis, ulcerative colitis, vasculitis, Wegener's granulomatosis, and psoriasis.

* * * * *